United States Patent
Gray et al.

(10) Patent No.: US 12,410,194 B2
(45) Date of Patent: Sep. 9, 2025

(54) POTENT AND SELECTIVE AZAINDOLE INHIBITORS OF CDK8 AND CDK19

(71) Applicant: Dana-Farber Cancer Institute, Inc., Boston, MA (US)

(72) Inventors: Nathanael S. Gray, Jamaica Plain, MA (US); John M. Hatcher, Boston, MA (US); Prasanna Sreevatsan, Watertown, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 777 days.

(21) Appl. No.: 17/756,413

(22) PCT Filed: Nov. 25, 2020

(86) PCT No.: PCT/US2020/062264
§ 371 (c)(1),
(2) Date: May 24, 2022

(87) PCT Pub. No.: WO2021/108581
PCT Pub. Date: Jun. 3, 2021

(65) Prior Publication Data
US 2023/0040191 A1    Feb. 9, 2023

Related U.S. Application Data

(60) Provisional application No. 62/940,632, filed on Nov. 26, 2019.

(51) Int. Cl.
*C07D 519/00* (2006.01)
*C07D 471/04* (2006.01)
*C07D 487/04* (2006.01)
*C07D 495/04* (2006.01)

(52) U.S. Cl.
CPC ......... *C07D 519/00* (2013.01); *C07D 471/04* (2013.01); *C07D 487/04* (2013.01); *C07D 495/04* (2013.01)

(58) Field of Classification Search
CPC .. C07D 519/00; C07D 471/04; C07D 487/04; C07D 495/04
See application file for complete search history.

(56) References Cited

U.S. PATENT DOCUMENTS

| | | |
|---|---|---|
| 6,407,103 B2 | 6/2002 | Nugiel et al. |
| 7,868,139 B2 | 1/2011 | Elson et al. |
| 11,285,144 B2 | 3/2022 | Sundberg et al. |
| 2007/0054916 A1 | 3/2007 | Patel et al. |
| 2011/0195951 A1 | 8/2011 | Graczyk et al. |
| 2011/0201599 A1 | 8/2011 | Bahceci et al. |
| 2012/0190659 A1 | 7/2012 | Corey et al. |
| 2013/0252930 A1 | 9/2013 | Chu et al. |
| 2017/0027956 A1 | 2/2017 | Hopkins et al. |
| 2018/0215763 A1 | 8/2018 | Wu et al. |
| 2020/0369715 A1 | 11/2020 | Gray et al. |

FOREIGN PATENT DOCUMENTS

| | | |
|---|---|---|
| WO | WO 2006/093993 A1 | 9/2006 |
| WO | WO 2012/092382 A2 | 7/2012 |
| WO | WO 2014/194201 A2 | 12/2014 |
| WO | WO 2015/100420 A1 | 7/2015 |

OTHER PUBLICATIONS

Mallinger et al., "Discovery of Potent, Selective, and Orally Bioavailable Small-Molecule Modulators of the Mediator Complex-Associated Kinases CDK8 and CCDK19", *Journal of Medicinal Chemistry* 59:1078-1101 (2016).
Czako et al., "Discovery of Potent and Practical Antiangiogenic Agents Inspired by Cortistatin A", *Journal of the American Chemical Society* 131:9014-9019 (2009).
Dale et al., "A selective chemical probe for exploring the role of CDK8 and CDK19 in human disease", *Nature Chemical Biology* 11(12):973-980 (Oct. 2015).
Elcombe et al., "Dectin-1 Regulates IL-10 Production via a MSK1/2 and CREB Dependent Pathway and Promotes the Induction of Regulatory Macrophage Markers", *PLOS One* 8(3):e60096 (Mar. 2013).
Hatcher et al., "Development of Highly Potent and Selective Steroidal Inhibitors and Degraders of CDK8", *ACS Medicinal Chemistry Letter* 9:540-545 (2018).
International Search Report and Written Opinion for International Application No. PCT/US2017/045387, mailed Oct. 24, 2017, 11 pages.
International Search Report and Written Opinion for International Application No. PCT/US2019/017747, mailed May 28, 2019, 12 pages.
International Search Report and Written Opinion for International Application No. PCT/US2020/062264, mailed Feb. 9, 2021, 8 pages.
Sidhu et al., "Small Molecule Tyrosine Kinase Inhibitors for the Treatment of Intestinal Inflammation", *Inflammatory Bowel Diseases* 17(12):2416-2426 (Mar. 2011).

*Primary Examiner* — Joseph K McKane
*Assistant Examiner* — Jalisa Holmes Ferguson
(74) *Attorney, Agent, or Firm* — Nielsen IP Law LLC

(57) ABSTRACT

Provided herein are compounds, pharmaceutical compositions comprising such compounds, and methods of using such compounds to treat diseases or disorders associated with CDK8 and/or CDK19.

27 Claims, 2 Drawing Sheets

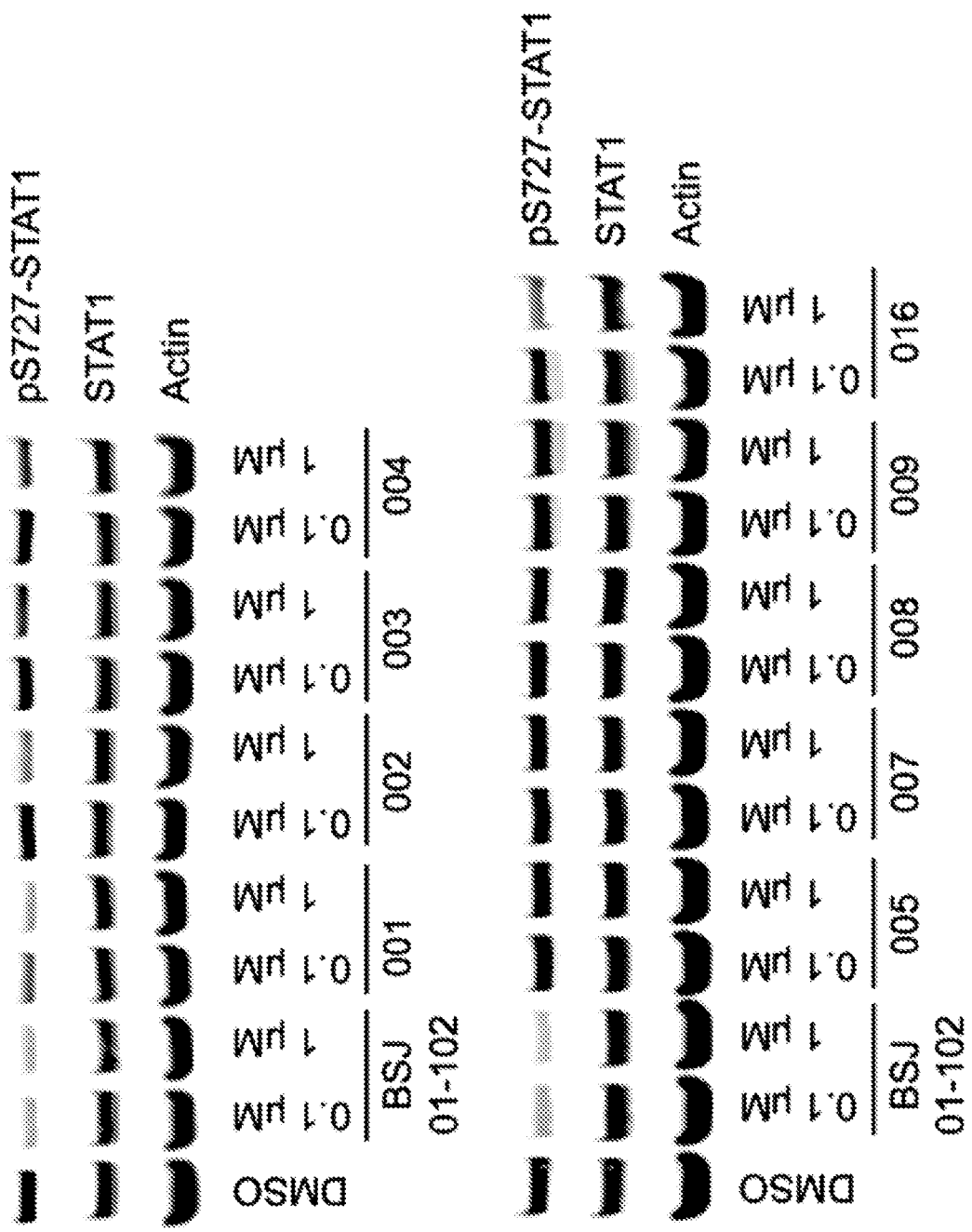

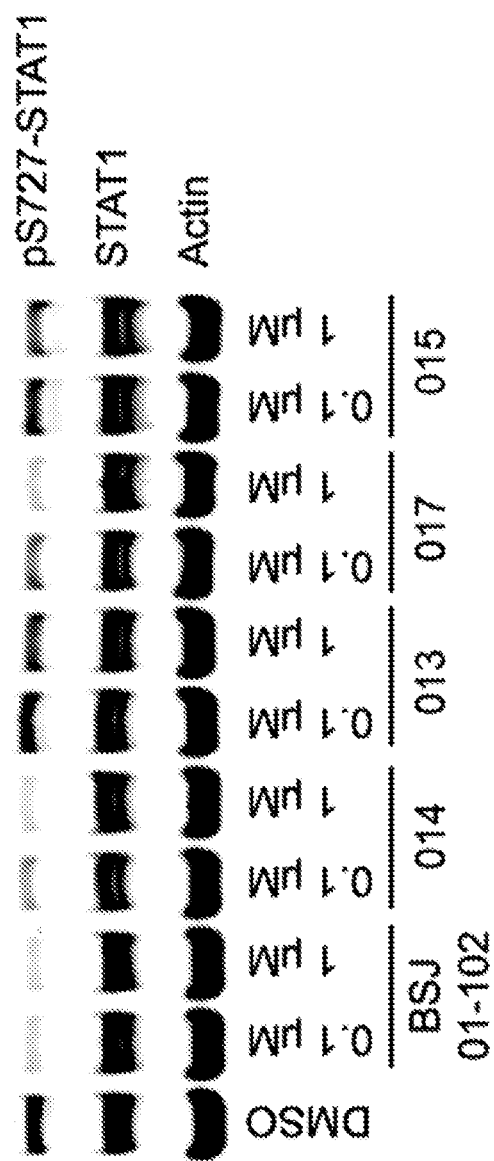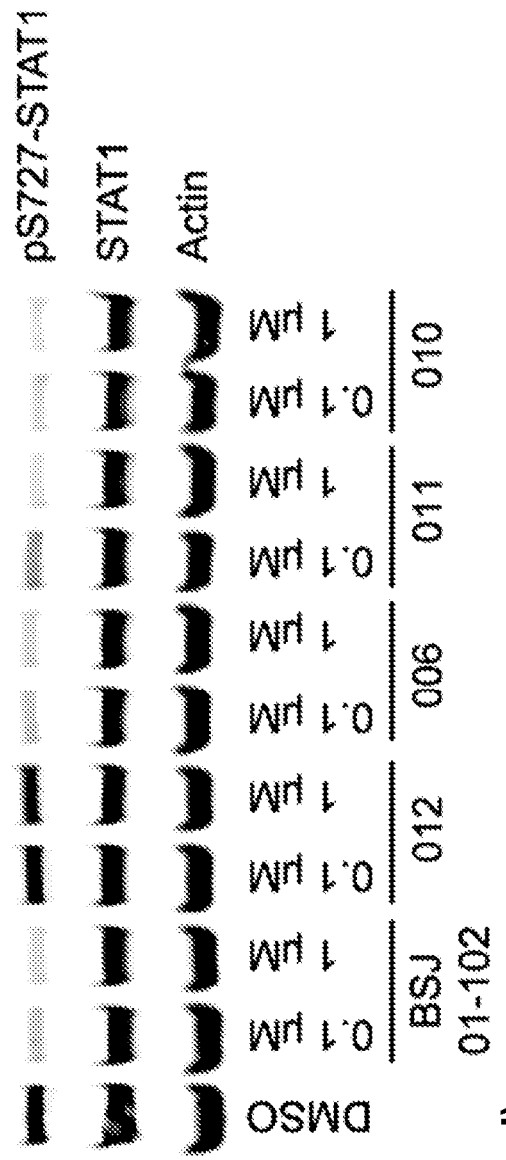
(Continued)

POTENT AND SELECTIVE AZAINDOLE INHIBITORS OF CDK8 AND CDK19

RELATED APPLICATIONS

This application is a 35 U.S.C. § 371 filing of International Patent Application No. PCT/US2020/062264, filed Nov. 25, 2020, which claims priority to U.S. provisional application No. 62/940,632 filed Nov. 26, 2019, the content of which is incorporated herein by reference in its entirety.

BACKGROUND

CDK8 is a cyclin-dependent kinase that forms part of the mediator complex, which regulates the transcriptional activity of RNA polymerase II, thereby regulating cellular proliferation and differentiation (Conaway, R. C., et al., *Trends in Biochemical Sciences* 2005, 30 (5), 250-255). CDK8 has been shown to modulate the transcriptional output from distinct transcription factors involved in oncogenic control including the Wnt/β-catenin pathway, Notch, p53, and TGF-β (Nemet, J., et al., Biochimie 2014, 97, 22-27 and Li. N., et al., *Nature Cell Biology* 2014, 16 (11), 1080-1091). Although the mechanism of how CDK8 activity regulates these various pathways remains unknown, CDK8 has been found to be amplified and overexpressed in colon and gastric cancer acting through the Wnt pathway and its key signaling molecule β-catenin (Kim, M. Y., et al., *International Journal of Oncology* 2011, 38 (5), 1375-1383). CDK8 gene expression also correlates with increased mortality in breast and ovarian cancers. Furthermore, CDK8 is overexpressed and essential for cell proliferation in melanoma.

Due to the importance of CDK8 in cancer cell proliferation, there remains a need for potent and selective CDK8 inhibitors.

SUMMARY

Provided herein are compounds and methods of using these compounds to treat disorders related to CDK8 and CDK19, including cancer, inflammatory disorders, and neurodegenerative disorders.

In an aspect, provided herein is a compound of Formula I:

(I)

or a pharmaceutically acceptable salt thereof;
wherein:
═ is an optional double bond;
A is a 5-8 membered heteroaryl;
B is CH or N;
D is $CR^5$ or N;
X is C or N;
Y is C or N;
Z is NH, S, or O;
$R^1$ and $R^2$, together with the carbon to which they are attached, form a 4-6 membered heterocyclic ring that is substituted one or two times with $R^4$;
$R^3$ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;
$R^4$ is selected from the group consisting of absent, ═O, amino, and hydroxy; and
$R^5$ is selected from the group consisting of hydrogen, halo, CN, $C_3$-$C_6$ cycloalkyl, and $C_1$-$C_6$ alkyl, wherein $C_1$-$C_6$ alkyl is optionally substituted by 1, 2, or 3 halo;
m is 1, 2, or 3.

In another aspect, provided herein is a method of inhibiting a kinase in a subject in need thereof comprising administering to the subject a therapeutically effective amount of a compound disclosed herein.

In yet another aspect, provided herein is a method of inhibiting cyclin-dependent kinase 8 (CDK8) and cyclin-dependent kinase 19 (CDK19) in a subject in need thereof comprising administering to the subject a therapeutically effective amount of a compound disclosed herein.

In still another aspect, provided herein is a method of treating a proliferative disease in a subject in need thereof comprising administering to the subject a therapeutically effective amount of a compound disclosed herein.

In an aspect, provided herein is a method of treating a cyclin-dependent kinase 8 (CDK8)-mediated disease and/or a cyclin-dependent kinase 19 (CDK19)-mediated disease in a subject in need thereof comprising administering to the subject a therapeutically effective amount of a compound of the present disclosure.

BRIEF DESCRIPTION OF THE DRAWINGS

FIG. 1 shows western blots indicating the inhibitory activity of the compounds disclosed herein.

DETAILED DESCRIPTION

Provided herein are compounds, or pharmaceutically acceptable salts thereof, that are useful in the treatment of cancer, inflammatory disorders, and neurodegenerative disorders in a subject in need thereof.

In a non-limiting aspect, these compounds can selectively inhibit cyclin-dependent kinase 8 (CDK8) and/or cyclin-dependent kinase 19 (CDK19). In a particular embodiment, the compounds provided herein are considered CDK8 and/or CDK19 inhibitors

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element"

means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated or caused by the state, disorder or disease being treated. In certain embodiments, the treatment comprises bringing into contact with CDK8 and/or CDK19 an effective amount of a compound provided herein for conditions related to cancers, hemoglobinopathies, or myelodysplastic syndrome.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts described herein include the conventional non-toxic salts of the parent compound formed, for example, from non-toxic inorganic or organic acids. The pharmaceutically acceptable salts discussed herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound disclosed herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound disclosed herein, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

The term "CDK" refers to cyclin-dependent kinases which are the families of protein kinases first discovered for their role in regulating the cell cycle. They are also involved in regulating transcription, mRNA processing, and the differentiation of nerve cells. CDKs phosphorylate their substrates on serines and threonines, so they are considered serine-threonine kinases.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. In an embodiment, $C_1$-$C_6$ alkyl groups are provided herein. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_6$ alkoxy groups are provided herein.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used here, the term "amino" refers to the group —N(R)$_2$, wherein R is independently, at each occurrence, hydrogen or $C_1$-$C_6$-alkyl as defined above. Examples of amino groups include —NH$_2$, dimethylamine, methylamine, diethylamine, ethylamine, and the like.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In an embodiment, 3-10 membered cycloalkyl groups are provided herein.

As used herein, the term "heterocycloalkyl" and "heterocyclic" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo-[2.1.1]hexanyl, 5-azabicyclo[2.1.1]hexanyl, 6-azabicyclo[3.1.1] heptanyl, 2-azabicyclo-[2.2.1]heptanyl, 3-azabicyclo[3.1.1]heptanyl, 2-azabicyclo[3.1.1]heptanyl, 3-azabicyclo-[3.1.0]hexanyl, 2-azabicyclo[3.1.0]hexanyl, 3-azabicyclo[3.2.1]octanyl, 8-azabicyclo[3.2.1]-octanyl, 3-oxa-7-azabicyclo[3.3.1] nonanyl, 3-oxa-9-azabicyclo[3.3.1]-nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]-nonanyl, and 8-oxabicyclo[3.2.1]octanyl. In an embodiment, 3-10 membered heterocycloalkyl groups are provided herein.

As used herein, the term "aromatic" refers to a carbocycle or heterocycle with one or more polyunsaturated rings and having aromatic character, i.e., having (4 n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. In an embodiment, 5-10 membered heteroaryl groups are provided herein.

It is to be understood that if an aryl, heteroaryl, cycloalkyl, or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thioenyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

In an aspect, provided herein is a compound of Formula I:

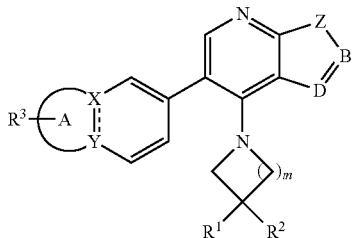

(I)

or a pharmaceutically acceptable salt thereof;
wherein:

==== is an optional double bond;

A is a 5-8 membered heteroaryl;

B is CH or N;

D is $CR^5$ or N;

X is C or N;

Y is C or N;

Z is NH, S, or O;

$R^1$ and $R^2$, together with the carbon to which they are attached, form a 4-6 membered heterocyclic ring that is substituted one or two times with $R^4$;

$R^3$ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;

$R^4$ is selected from the group consisting of absent, =O, amino, and hydroxy;

$R^5$ is selected from the group consisting of hydrogen, halo, CN, $C_3$-$C_6$ cycloalkyl, and $C_1$-$C_6$ alkyl, wherein $C_1$-$C_6$ alkyl is optionally substituted by 1, 2, or 3 halo; and m is 1, 2, or 3.

In an embodiment of Formula I, only one of Z, B, or D is a nitrogen atom. In another embodiment of Formula I, two of Z, B, or D are a nitrogen atom.

In an embodiment, the compound of Formula I is a compound of Formula II:

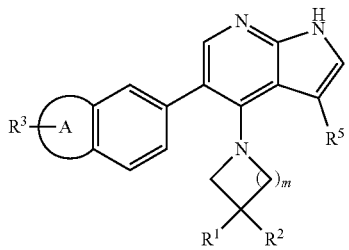

(II)

or a pharmaceutically acceptable salt thereof.

In another embodiment, $R^1$ and $R^2$, together with the carbon to which they are attached, form piperidinone, pyrrolidinone, azetidinone, oxazolidinone, imidazolidine-dione, dihydro-thiazole, dihydro-oxazole, dihydro-pyrrole, dihydro-imidazolone, or morpholinone.

In yet another embodiment, A is a 5-8 membered heteroaryl having one or two nitrogen atoms. In still another embodiment, A is selected from the group consisting of pyrazole, thiazole, imidazole, and triazole.

In another aspect, provided herein is a compound of Formula III:

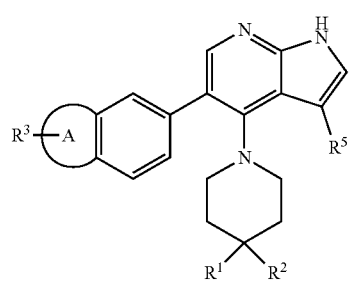

(III)

or a pharmaceutically acceptable salt thereof;
wherein:

A is a 5-8 membered heteroaryl;

$R^1$ and $R^2$, together with the carbon to which they are attached, form a 4-6 membered heterocyclic ring that is substituted one or two times with $R^4$;

$R^3$ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;

$R^4$ is selected from the group consisting of absent, =O, amino, and hydroxy; and $R^5$ is selected from the group consisting of hydrogen, halo, CN, $C_3$-$C_6$ cycloalkyl, and $C_1$-$C_6$ alkyl, wherein $C_1$-$C_6$ alkyl is optionally substituted by 1, 2, or 3 halo.

In an embodiment, the compound of Formula III is a compound of Formula IIIa:

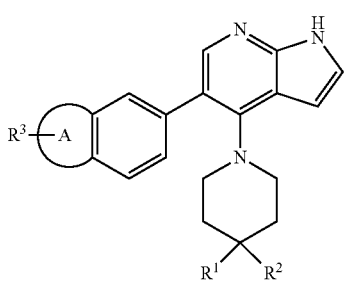

(IIIa)

or a pharmaceutically acceptable salt thereof.

In another embodiment, the compound of Formula III is a compound of Formula IV:

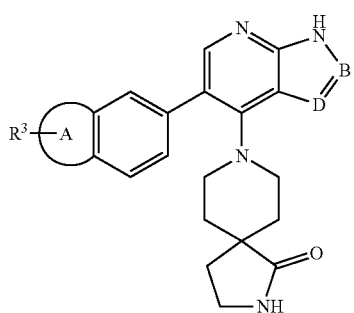

(IV)

or a pharmaceutically acceptable salt thereof.

In yet another embodiment, the compound of Formula I is a compound of Formula V:

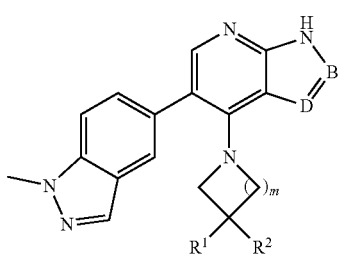

(V)

or a pharmaceutically acceptable salt thereof.

In still another embodiment, B and D are both CH. In an embodiment, B is N and D is CH. In another embodiment, B is CH and D is N. In yet another embodiment, C is CH and D is $CR^5$.

In an embodiment, the compound of Formula I is a compound of Formula VI:

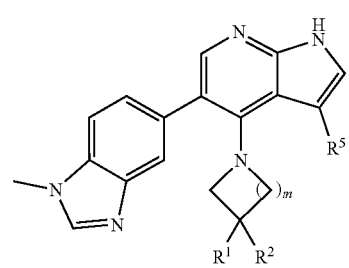

(VI)

or a pharmaceutically acceptable salt thereof.

In yet another embodiment, the compound of Formula I is a compound of formula VII:

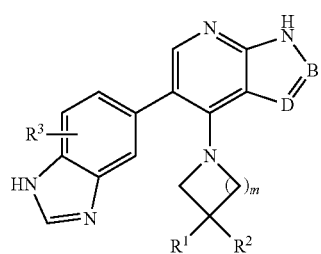

(VII)

or a pharmaceutically acceptable salt thereof.

In another aspect, provided herein is a compound of Formula VIII:

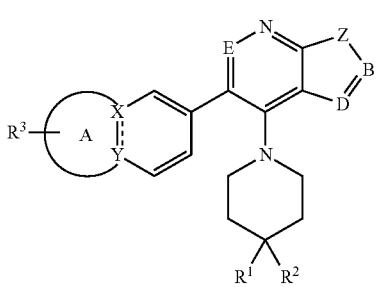

(VIII)

or a pharmaceutically acceptable salt thereof;
wherein:
==== is an optional double bond;
A is a 5-8 membered heteroaryl;
B and D are each independently $CR^5$ or N;
E is CH or N;
X is C or N;
Y is C or N;
Z is NH, S, or O;
$R^1$ and $R^2$, together with the carbon to which they are attached, form a 4-6 membered heterocyclic ring that is substituted one or two times with $R^4$;
$R^3$ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;
$R^4$ is selected from the group consisting of absent, =O, amino, and hydroxy; and each $R^5$ is independently selected from the group consisting of hydrogen, halo, CN,
$C_3$-$C_6$ cycloalkyl, and $C_1$-$C_6$ alkyl, wherein $C_1$-$C_6$ alkyl is optionally substituted by 1, 2, or 3 halo.

In an embodiment of Formula VIII, only one of Z, B, or D is a nitrogen atom. In another embodiment of Formula VIII, two of Z, B, or D are a nitrogen atom.

In an embodiment, the compound of Formula VIII is a compound of Formula VIIIa:

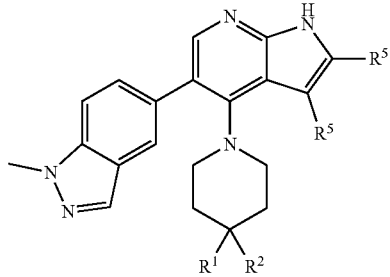

(VIIIa)

or a pharmaceutically acceptable salt thereof.

In another embodiment, the compound of Formula VIII is a compound of Formula VIIIb:

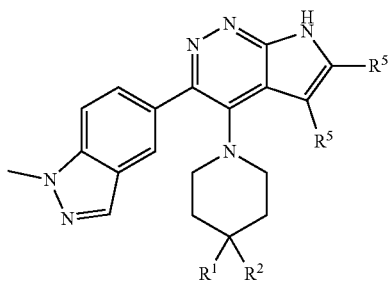

(VIIIb)

or a pharmaceutically acceptable salt thereof.

In yet another embodiment of the formulae provided herein, A is a 5-8 membered heteroaryl having one or two nitrogen atoms. In still another embodiment, A is selected from the group consisting of pyrazole, thiazole, imidazole, and triazole.

In an embodiment of the formulae provided herein, $R^1$ and $R^2$, together with the carbon to which they are attached, form a 4-6 membered heterocyclic ring optionally substituted with =O, $NH_2$, or both =O and $NH_2$. In an embodiment, the 4-6 membered heterocyclic ring contains one nitrogen. In another embodiment, the 4-6 membered heterocyclic ring contains two nitrogen atoms.

In another embodiment of Formula I, II, III, IIIa, V, VI, VII, VIII, VIIIa, and VIIIb, $R^1$ and $R^2$, together with the atoms to which they are attached, form the following heterocyclic rings

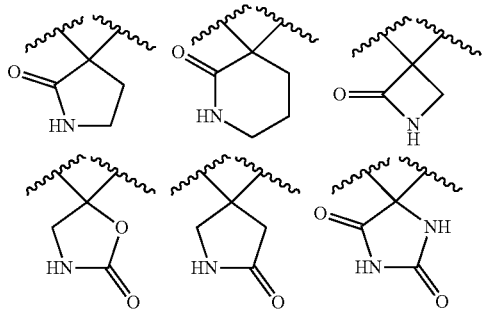

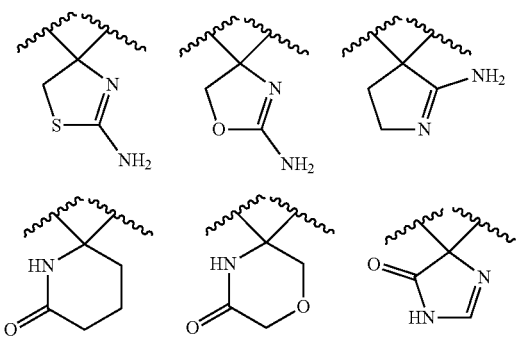

wherein the heterocyclic rings are optionally substituted with or two $R^4$.

In an embodiment, $R^4$ is =O. In another embodiment, $R^2$ is $NH_2$.

In another embodiment, the compound of the Formulae provided herein is selected from the group consisting of a compound from Table 1.

TABLE 1

| Compound No. | Structure |
| --- | --- |
| 001 | 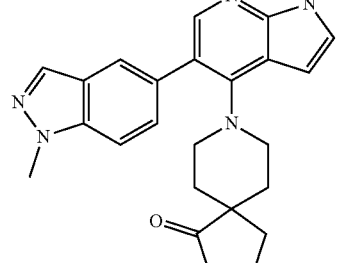 |
| 002 | 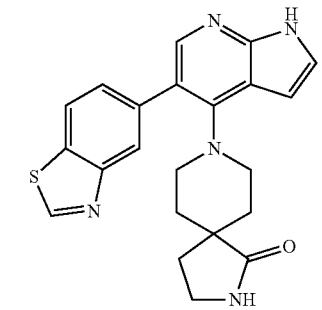 [SMILES: O=C1NCCC12CCN(c1c(-c3ccc4scnc4c3)cnc3[nH]ccc13)CC2] |
| 003 | 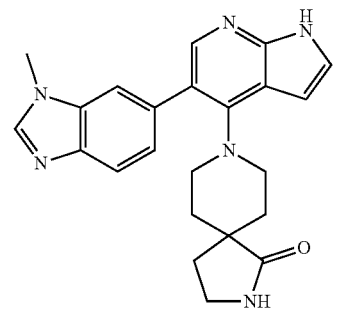 [SMILES: Cn1cnc2ccc(-c3cnc4[nH]ccc4c3N3CCC4(CCNC4=O)CC3)cc21] |

TABLE 1-continued

| Compound No. | Structure |
|---|---|
| 004 | (structure) |
| 005 | (structure) |
| 006 | (structure) |
| 007 | (structure) |
| 008 | (structure) |
| 009 | (structure) |
| 010 | (structure) |
| 011 | (structure) |
| 012 | (structure) |
| 013 | (structure) |

TABLE 1-continued

| Compound No. | Structure |
|---|---|
| 014 | 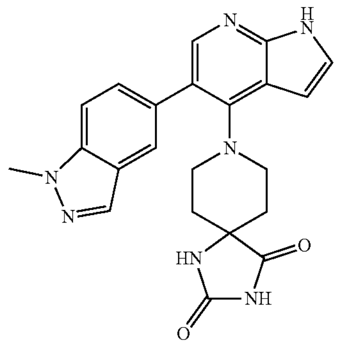 |
| 015 | 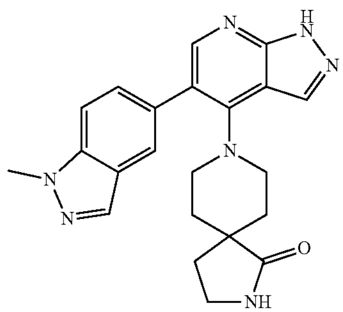 |
| 016 | 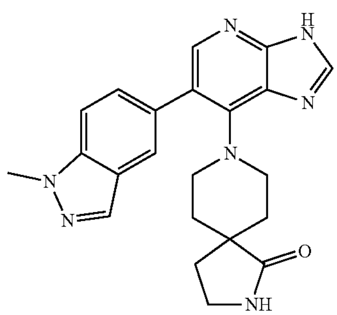 [SMILES: Cn1ncc2cc(-c3cnc4[nH]cnc4c3N3CCC4(CCNC4=O)CC3)ccc21] |
| 017 | 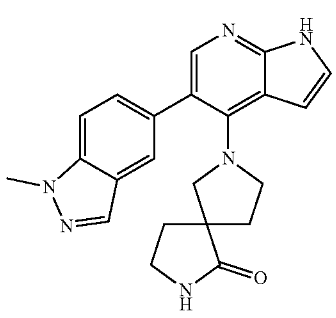 [SMILES: Cn1ncc2cc(-c3cnc4[nH]ccc4c3N3CCC4(CCNC4=O)C3)ccc21] |
| 018 | 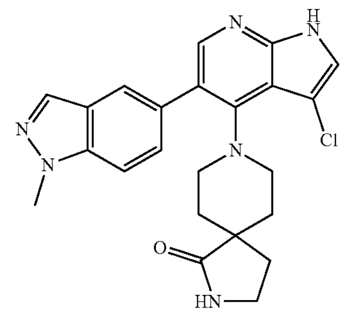 |
| 019 | 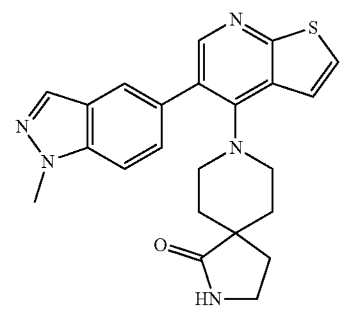 |
| 020 | 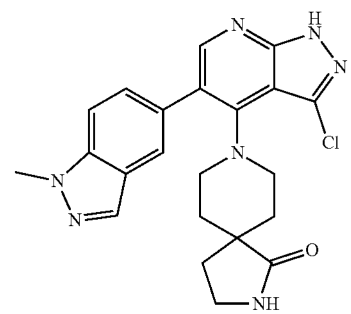 [SMILES: Cn1ncc2cc(-c3cnc4[nH]nc(Cl)c4c3N3CCC4(CCNC4=O)CC3)ccc21] |
| 021 | | or a pharmaceutically acceptable salt thereof.

In an aspect, provided herein is a pharmaceutical composition comprising any one of the compounds described herein, or a pharmaceutically acceptable salt thereof, together with a pharmaceutically acceptable carrier.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a $^2$H (i.e., deuterium) isotope.

In still another embodiment, substitution with positron emitting isotopes, such as $^{11}$C, 18F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds provided herein can be used in a method of treating a disease or condition in a subject, said method comprising administering to the subject in need thereof a compound provided herein, or pharmaceutically acceptable salt thereof, or a pharmaceutical composition comprising a compound provided herein, or pharmaceutically acceptable salt thereof.

In an aspect, provided herein is a method of inhibiting a kinase in a subject in need thereof comprising administering to the subject a therapeutically effective amount of a compound disclosed herein.

In an embodiment, the kinase is cyclin-dependent kinase 8 (CDK8). In another embodiment, the kinase is cyclin-dependent kinase 19 (CDK19).

In another aspect, provided herein is a method of inhibiting cyclin-dependent kinase 8 (CDK8) and cyclin-dependent kinase 19 (CDK19) in a subject in need thereof comprising administering to the subject a therapeutically effective amount of a compound disclosed herein.

In yet another aspect, provided herein is method of treating a proliferative disease in a subject in need thereof comprising administering to the subject a therapeutically effective amount of a compound of the present disclosure.

In still another aspect, provided herein is a method of treating a cyclin-dependent kinase 8 (CDK8)-mediated disease and/or a cyclin-dependent kinase 19 (CDK19)-mediated disease in a subject in need thereof comprising administering to the subject a therapeutically effective amount of a compound of the present disclosure.

In an embodiment, the disease is cancer.

In another embodiment, the cancer is selected from the group consisting of lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma, lymphomas, myelomas, or solid tumors.

In yet another embodiment, the cancer is selected from the group consisting of leukemia, lymphoma, colorectal cancer, epithelial call-derived neoplasia (epithelial carcinoma), basal cell carcinoma, adenocarcinoma, gastrointestinal cancer, lip cancer, mouth cancer, esophageal cancer, small bowel cancer, bladder cancer, cervical cancer, squamus cell and/or basal cell cancers, renal cell carcinoma, and B-Cell Lymphoma.

In an embodiment, the cancer is breast cancer, ovarian cancer, or melanoma.

In still another embodiment, the leukemia is selected from the group consisting of chronic myelogenous leukemia (CML), acute myeloid leukemia (AML) and acute promyelocytic leukemia (APL).

In an embodiment, the disease is selected from the group consisting of inflammation, arthritis, rheumatoid arthritis, spondylarthropathies, gouty arthritis, osteoarthritis, and juvenile arthritis.

In another embodiment, the disease is selected from the group consisting of systemic lupus erythematosus (SLE), skin-related conditions, psoriasis, eczema, burns, dermatitis, neuroinflammation, allergy, pain, neuropathic pain, and fever.

In yet another embodiment, the disease is selected from the group consisting of pulmonary disorders, lung inflammation, adult respiratory distress syndrome, pulmonary sarcoidosis, asthma, silicosis, chronic pulmonary inflammatory disease, and chronic obstructive pulmonary disease (COPD).

In still another embodiment, the disease is selected from the group consisting of cardiovascular disease, arteriosclerosis, myocardial infarction, post-myocardial infarction indications, thrombosis, congestive heart failure, cardiac reperfusion injury, complications associated with hypertension and/or heart failure, vascular organ damage, restenosis, cardiomyopathy, ischemic stroke, hemorrhagic stroke, and reperfusion injury.

In an embodiment, the disease is selected from the group consisting of liver disease and nephritis, gastrointestinal conditions, inflammatory bowel disease, Crohn's disease, gastritis, irritable bowel syndrome, ulcerative colitis, ulcerative diseases, and gastric ulcers.

In another embodiment, the disease is selected from the group consisting of viral infections, bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction, and allograft rejections.

In an embodiment, the disease is a neurodegenerative disorder. In another embodiment, the neurodegenerative disorder is selected from the group consisting of Alzheimer's disease, Parkinson's disease, Huntington's disease, amyotrophic lateral sclerosis, spinal cord injury, and peripheral neuropathy.

In yet another embodiment, the method involves the administration of a therapeutically effective amount of a compound provided herein, or a pharmaceutically acceptable salt thereof, to a subject (including, but not limited to a human or animal) in need of treatment (including a subject identified as in need).

Administration/Dosage/Formulations

In another aspect, provided herein is a pharmaceutical composition comprising at least one compound disclosed herein, together with a pharmaceutically acceptable carrier. Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated using one or more pharmaceutically acceptable excipients or carriers. In one embodiment, the pharmaceutical compositions provided herein comprise a therapeutically effective amount of a disclosed compound and a pharmaceutically acceptable carrier.

Routes of administration of any of the compositions discussed herein include oral, nasal, rectal, intravaginal, parenteral, buccal, sublingual or topical. The compounds may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations

B$_2$pin$_2$ bis(pinacolato)diboron
cataCXium A di(1-adamantyl)-n-butylphosphine
DCM dichloromethane/methylene chloride
DMF dimethylformamide
DMSO dimethylsulfoxide
Dppf 1,1'-bis(diphenylphosphino)ferrocene
Et$_3$N triethylamine
EtOAc ethyl acetate
F.C. flash chromatography
mCPBA m-chloroperoxybenzoic acid
MW microwave
NMP N-methyl-2-pyrrolidone
r.t. room temperature
SEM 2-(trimethylsilyl)ethoxymethyl
tBuXPhos 2-di-tert-butylphosphino-2',4',6'-triisopropyl-biphenyl
TFA trifluoroacetic acid
THF tetrahydrofuran Synthesis Procedures Example 1—Synthetic Procedure A

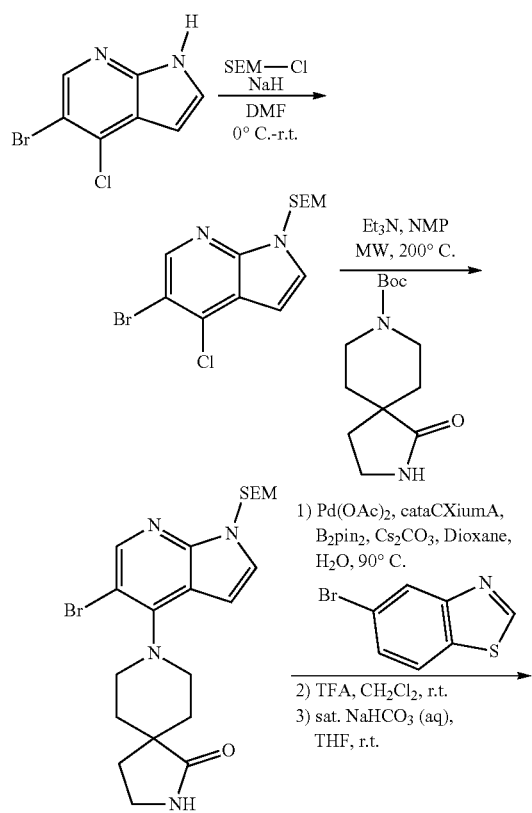

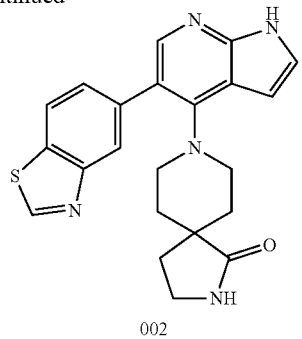

5-bromo-4-chloro-1-((2-(trimethylsilyl)ethoxy)methyl)-1H-pyrrolo[2,3-b]pyridine

To a solution of 5-bromo-4-chloro-1H-pyrrolo[2,3-b]pyridine (5.0 g, 21.60 mmol) in DMF (25 mL) at 0° C., was added 60% NaH (0.95 g, 23.7 mmol), stirred at r.t. for 30 minutes, following which was added SEM-Cl (4.59 mL, 25.92 mmol) dropwise and set to stir at r.t. until consumption of the starting material. The reaction was quenched with water, diluted with ethyl acetate, the aqueous layer was extracted with ethyl acetate (3×30 mL), the organic layers were combined, washed with brine, dried over Na$_2$SO$_4$ and concentrated. The crude was purified by flash chromatography using a gradient of 5% to 20% ethyl acetate in hexanes to give a yellow solid (6.50 g, 17.96 mmol) in 83.1% yield. MS (ESI) m/z 362.96 (M+H)$^+$. $^1$H NMR (500 MHz, DMSO-d$_6$) δ 8.48 (s, 1H), 7.83 (d, J=3.5 Hz, 1H), 6.63 (d, J=3.5 Hz, 1H), 5.62 (s, 2H), 3.50 (t, J=5 Hz, 2H), 0.80 (t, J=5 Hz, 2H).

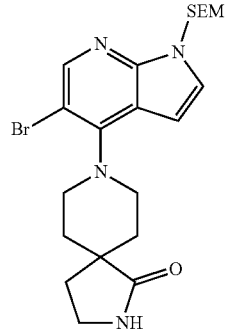 [SMILES: C[Si](C)(C)CCOCn1ccc2c(N3CCC4(CCNC4=O)CC3)c(Br)cnc21]

8-(5-bromo-1-((2-(trimethylsilyl)ethoxy)methyl)-1H-pyrrolo[2,3-b]pyridin-4-yl)-2,8 diazaspiro[4.5]decan-1-one To a microwave vial were added, 5-bromo-4-chloro-1-((2-(trimethylsilyl)ethoxy)-methyl)-1H-pyrrolo[2,3-b]pyridine (2 g, 5.52 mmol), tert-butyl 1-oxo-2,8-diazaspiro[4.5]-decane-8-carboxylate (2.21 g, 14.37 mmol) and triethylamine (7.71 mL, 55.28 mmol). NMP (20 mL) was added, the vial was capped and heated in a microwave reactor at 200° C. for 2 h. The mixture was quenched with H₂O, the aqueous layer was extracted with ethyl acetate (3×30 mL), the combined organic layers were washed with H₂O, brine, dried over Na₂SO₄ and concentrated. The crude was purified by F.C. using a gradient 10%-100% ethyl acetate in hexanes to give a brown oil (1.23 g, 72% yield b.r.s.m). MS (ESI) m/z 481.18 (M+H)⁺. ¹H NMR (500 MHz, DMSO-d₆) δ 8.22 (s, 1H), 7.62 (s, 1H), 7.53 (d, J=5 Hz, 1H), 6.74 (d, J=5 Hz, 1H), 5.55 (s, 2H), 3.62 (d, J=15 Hz, 2H), 3.49 (t, J=10 Hz, 2H), 3.25-3.23 (m, 2H), 3.22 (t, J=10 Hz, 2H), 2.08 (t, J=10 Hz, 2H), 1.93-1.87 (m, 2H), 1.50 (d, J=15 Hz, 2H), 0.80 (t, J=10 Hz, 2H).

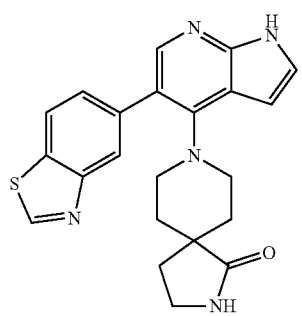 [SMILES: O=C1NCCC12CCN(c1c(-c3ccc4scnc4c3)cnc3[nH]ccc13)CC2]

Compound 002: 8-(5-(benzo[d]thiazol-5-yl)-1H-pyrrolo[2,3-b]pyridin-4-yl)-2,8-diazaspiro[4.5]decan-1-one To a degassed solution of 8-(5-bromo-1-((2-(trimethylsilyl)ethoxy)methyl)-1H-pyrrolo[2,3-b]pyridin-4-yl)-2,8 diazaspiro[4.5]decan-1-one (75 mg, 0.15 mmol), 5-bromo-benzo[d]thiazole (43.5 mg, 0.20 mmol), bis(pinacolato)diboron (59.58 mg, 0.23 mmol) and Cs₂CO₃ (255.5 mg, 0.78 mmol) in 1,4-dioxane (0.8 mL) and H₂O (0.2 mL) was added Pd(OAc)₂ (5.27 mg, 0.023 mmol) and CataCXium A (16.82 mg, 0.046 mmol). The mixture was backfilled with N₂ and stirred at 90° C. for 1 h until completion of the reaction. The mixture was then cooled to room temperature, quenched with water. The aqueous layer was extracted with ethyl acetate (3×10 mL), the organic layers were combined and washed with brine, dried over Na₂SO₄ and concentrated. The crude was dissolved in DCM (10 mL), TFA (1 mL) was added, stirred at rt for 1 h until consumption of starting material, the solvent was removed, and the residue dissolved in THF (5 mL). Saturated (aq.) NaHCO₃ (2 mL) was added and the mixture stirred for 6 hours at rt. The mixture was quenched with H₂O and the aqueous layer was extracted with ethyl acetate (3×5 mL). The combined organic layers were washed with H₂O, brine, dried over MgSO₄ and condensed. The crude was dissolved in DMSO, filtered and purified by reverse phase HPLC using a gradient of 1%-60% acetonitrile in H₂O to give 9 mg of the desired product in 9.6% yield. MS (ESI) m/z: 404.8 (M+H)+. ¹H NMR (500 MHz, DMSO-de) δ 9.46 (s, 1H), 8.27 (s, 1H), 8.22 (s, 1H), 8.05 (s, 1H), 7.64 (d, J=10 Hz, 1H), 7.57 (s, 1H), 7.48 (s, 1H), 6.84 (s, 1H), 3.67-3.66 (m, 2H), 3.19-3.14 (m, 2H), 3.12 (t, J=10 Hz, 2H), 1.93 (t, J=10 Hz, 2H), 1.64-1.61 (m, 2H), 1.32-1.29 (m, 2H).

The following compounds were prepared in a similar procedure as shown in Scheme 1 for compound 002.

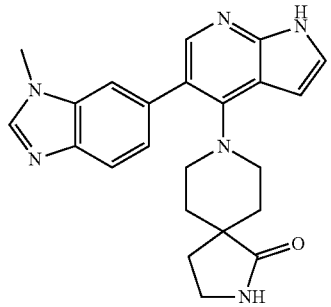 [SMILES: Cn1cnc2ccc(-c3cnc4[nH]ccc4c3N3CCC4(CCNC4=O)CC3)cc21]

Compound 001: 8-(5-(1-methyl-1H-benzo[d]imidazol-6-yl)-1H-pyrrolo[2,3-b]pyridin-4-yl)-2,8-diazaspiro[4.5]decan-1-one.

Prepared according to the same procedure used for 002 to give 16 mg of the desired product in 15.0% yield. MS (ESI) m/z: 401.2 (M+H)⁺ ¹H NMR (500 MHz, DMSO-d₆) δ 9.14 (s, 1H), 8.07 (s, 1H), 8.05 (s, 1H), 7.90 (d, J=5 Hz, 1H), 7.62 (d, J=5 Hz, 1H), 7.58 (s, 1H), 7.50 (s, 1H), 6.86 (s, 1H), 4.07 (s, 3H), 3.62-3.59 (m, 2H), 3.21-3.17 (m, 2H), 3.12 (t, J=10 Hz, 2H), 1.95 (t, J=10 Hz, 2H), 1.65-1.61 (m, 2H), 1.27-1.25 (m, 2H).

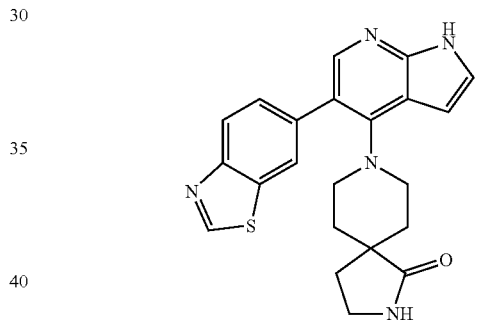

Compound 004: 8-(5-(benzo[d]thiazol-6-yl)-1H-pyrrolo[2,3-b]pyridin-4-yl)-2,8-diazaspiro[4.5]decan-1-one Prepared according to the same procedure used for 002 to give 16 mg of the desired product in 15.0% yield. MS (ESI) m/z: 404.14 (M+H)⁺ ¹H NMR (500 MHz, DMSO-d₆) δ 9.43 (s, 1H), 8.31 (s, 1H), 8.17 (d, J=10 Hz, 1H), 8.04 (s, 1H), 7.68 (d, J=10 Hz, 1H), 7.56 (s, 1H), 7.47 (s, 1H), 6.82 (s, 1H), 3.18-3.16 (m, 2H), 3.13-3.10 (m, 2H), 1.93 (t, J=5 Hz, 2H), 1.66-1.60 (m, 2H), 1.30-1.28 (m, 2H).

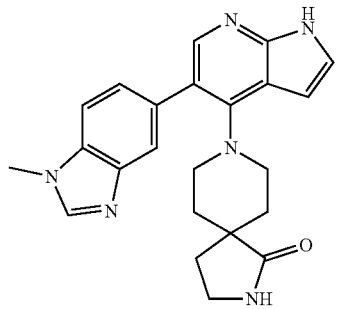 [SMILES: Cn1cnc2cc(-c3cnc4[nH]ccc4c3N3CCC4(CCNC4=O)CC3)ccc21]

Compound 005: 8-(5-(1-methyl-1H-benzo[d]imidazol-5-yl)-1H-pyrrolo[2,3-b]pyridin-4-yl)-2,8-diazaspiro[4.5]decan-1-one Prepared according to the same procedure used for 002 to give 7.3 mg of the desired product in 11.65% yield. MS (ESI) m/z: 401.2 (M+H)+ ¹H NMR (500 MHz, DMSO-$d_6$) δ 9.15 (s, 1H), 8.01 (s, 1H), 7.95 (d, J=5 Hz, 1H), 7.64 (d, J=5 Hz, 1H), 7.58 (s, 1H), 7.50-7.49 (m, 1H), 6.85 (s, 1H), 4.04 (s, 3H), 3.66-3.63 (m, 2H), 3.18-3.16 (m, 2H), 3.12 (t, J=5 Hz, 2H), 1.93 (t, J=5 Hz, 2H), 1.66-1.60 (m, 2H), 1.32-1.29 (m, 2H).

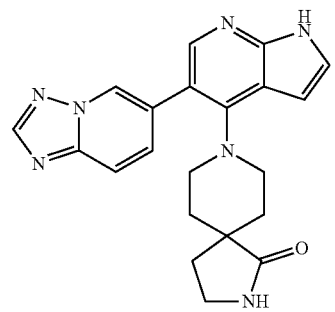 [SMILES: O=C1NCCC12CCN(c1c(-c3ccc4ncnn4c3)cnc3[nH]ccc13)CC2]

Compound 007: 8-(5-([1,2,4]triazolo[1,5-a]pyridin-6-yl)-1H-pyrrolo[2,3-b]pyridin-4-yl)-2,8-diazaspiro[4.5]decan-1-one.

Prepared according to the same procedure used for 002 to give 4.8 mg of the desired product in 13.65% yield. MS (ESI) m/z: 388.12 (M+H)+

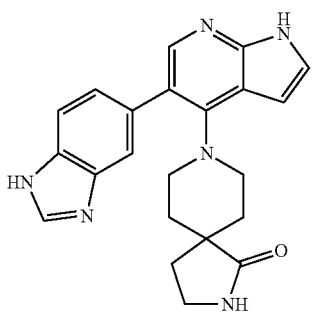 [SMILES: O=C1NCCC12CCN(c1c(-c3ccc4[nH]cnc4c3)cnc3[nH]ccc13)CC2]

Compound 008: 8-(5-(1H-benzo[d]imidazol-5-yl)-1H-pyrrolo[2,3-b]pyridin-4-yl)-2,8-diazaspiro[4.5]decan-1-one.

Prepared according to the same procedure used for 002 to give 11.0 mg of the desired product in 13.65% yield. MS (ESI) m/z: 387.21 (M+H)+ ¹H NMR (500 MHz, DMSO-$d_6$) δ 9.23 (s, 1H), 8.01 (s, 1H), 7.89 (s, 1H), 7.88 (d, J=10 Hz, 1H), 7.61 (d, J=10 Hz, 1H), 7.57 (s, 1H), 7.49-7.48 (m, 1H), 6.83 (s, 1H), 3.17-3.15 (m, 2H), 3.12 (t, J=5 Hz, 2H), 1.93 (t, J=5 Hz, 2H), 1.64-1.59 (m, 2H), 1.30-1.28 (m, 2H).

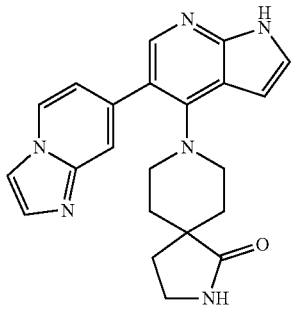 [SMILES: O=C1NCCC12CCN(c1c(-c3ccn4ccnc4c3)cnc3[nH]ccc13)CC2]

Compound 009: 8-(5-(imidazo[1,2-a]pyridin-7-yl)-1H-pyrrolo[2,3-b]pyridin-4-yl)-2,8-diazaspiro[4.5]decan-1-one.

Prepared according to the same procedure used for 002 to give 4.8 mg of the desired product in 13.65% yield. MS (ESI) m/z: 387.16 (M+H)+

Example 2—Synthetic Procedure B

Scheme 2.

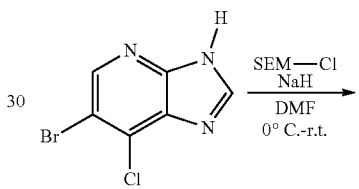

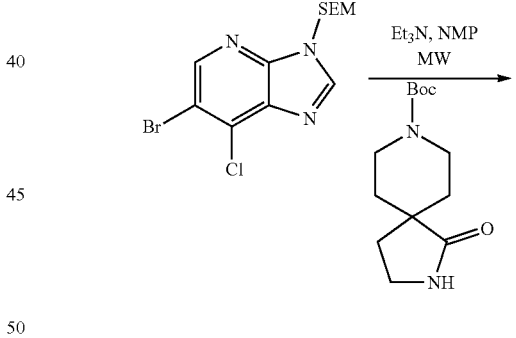

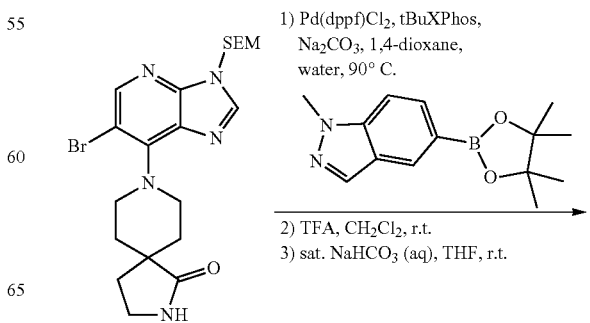

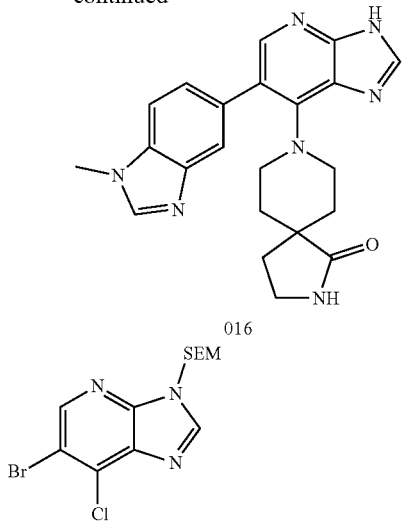

016

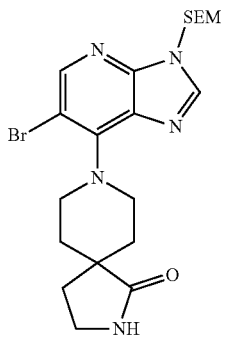 [SMILES: C[Si](C)(C)CCOCn1cnc2c(N3CCC4(CCNC4=O)CC3)c(Br)cnc21]

6-bromo-7-chloro-3-((2-(trimethylsilyl)ethoxy)methyl)-3H-imidazo[4,5-b]pyridine

Prepared according to the same protocol described in Scheme 1 to give 5.5 g of the desired product in 73.3% yield. MS (ESI) m/z: 363.78 (M+H)+.

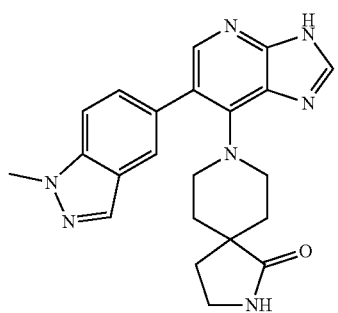 [SMILES: Cn1ncc2cc(-c3cnc4[nH]cnc4c3N3CCC4(CCNC4=O)CC3)ccc21]

8-(6-bromo-3-((2-(trimethylsilyl)ethoxy)methyl)-3H-imidazo[4,5-b]pyridin-7-yl)-2,8-diazaspiro[4.5]decan-1-one Prepared according to the same protocol described in Scheme 1 to give 236 mg of the desired product in 89.2% yield. MS (ESI) m/z: 479.72 (M+H)+

Compound 016: 8-(6-(1-methyl-1H-indazol-5-yl)-3H-imidazo[4,5-b]pyridin-7-yl)-2,8-diazaspiro[4.5]decan-1-one To a degassed solution of 8-(6-bromo-3-((2-(trimethylsilyl)ethoxy)methyl)-3H-imidazo[4,5-b]pyridin-7-yl)-2,8-diazaspiro[4.5]decan-1-one (150 mg, 0.30 mmol), 1-methyl-5-(4,4,5,5-tetramethyl-1,3,2-dioxaborolan-2-yl)-1H-indazole (104.46 mg, 0.41 mmol), Na₂CO₃ solution (aq.) (0.78 mL, 1.56 mmol) in 1,4-dioxane (1.5 mL) was added Pd(dppf)Cl₂ (27.42 mg, 0.036 mmol) and tBuXPhos (23.85 mg, 0.054 mmol). The mixture was backfilled with N₂ and stirred at 90° C. for 1 h until completion of the reaction. The reaction mixture was then cooled to room temperature and quenched with water. The aqueous layer was extracted with ethyl acetate (3×10 mL), the organic layers were combined and washed with brine, dried over Na₂SO₄ and concentrated. The crude was dissolved in DCM (10 mL), TFA (1 mL) was added, stirred at rt for 1 h until consumption of starting material. The solvent was removed, and the residue dissolved in THF (5 mL). Saturated (aq.) NaHCO₃ (2 mL) was added and the mixture stirred for 6 hours at rt. The mixture was quenched with H₂O and the aqueous layer was extracted with ethyl acetate (3×5 mL). The combined organic layers were washed with H₂O, brine, dried over MgSO₄ and condensed. The crude was dissolved in DMSO, filtered and purified by reverse phase HPLC using a gradient of 1%-60% acetonitrile in H₂O to give 10 mg of the desired product in 24.9% yield. MS (ESI) m/z: 401.47 (M+H)+.

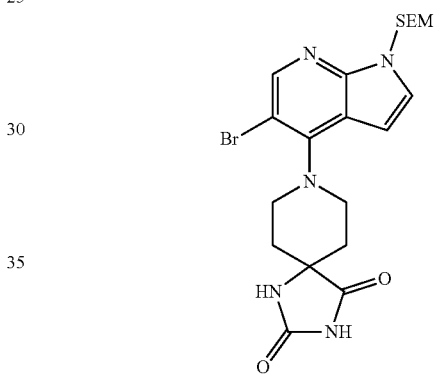

8-(5-bromo-1-((2-(trimethylsilyl)ethoxy)methyl)-1H-pyrrolo[2,3-b]pyridin-4-yl)-1,3,8-triazaspiro[4.5]decane-2,4-dione Prepared according to the same procedure in Scheme 1 to give 210 mg of the desired product in 76.8% yield (b.r.s.m.). MS (ESI) m/z: 496.13 (M+H)+ ¹H NMR (500 MHz, DMSO-d₆) δ 10.74 (s, 1H), 8.66 (s, 1H), 8.25 (s, 1H), 7.58 (d, J=5 Hz, 1H), 6.73 (d, J=5 Hz, 1H), 5.56 (s, 2H), 3.58-3.56 (m, 2H), 3.51-3.48 (m, 2H), 2.07-2.01 (m, 2H), 1.72 (d, J=15 Hz, 1H), 0.80 (t, J=10 Hz. 2H).

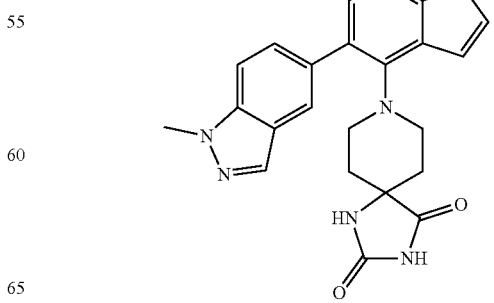

Compound 014: 8-(5-(1-methyl-1H-indazol-5-yl)-1H-pyrrolo[2,3-b]pyridin-4-yl)-1,3,8-triazaspiro[4.5]decane-2,4-dione Prepared according to the same protocol described in Scheme 2 to give 8 mg of the desired product in 3.73% yield. MS (ESI) m/z: 415.46 (M+H)+

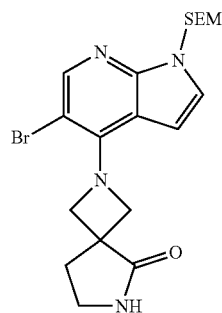 [SMILES: C[Si](C)(C)CCOCn1ccc2c(N3CC4(CCNC4=O)C3)c(Br)cnc21]

2-(5-bromo-1-((2-(trimethylsilyl)ethoxy)methyl)-1H-pyrrolo[2,3-b]pyridin-4-yl)-2,6-diazaspiro[3.4]octan-5-one Prepared according to the same protocol described in Scheme 1 to give 123 mg of the desired product in 82.1% yield (b.r.s.m.). MS (ESI) m/z: 450.74 (M+H)+

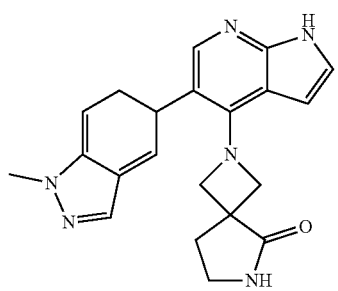 [SMILES: Cn1ncc2c1=CCC(c1cnc3[nH]ccc3c1N1CC3(CCNC3=O)C1)C=2]

Compound 013: 2-(5-(1-methyl-1H-indazol-5-yl)-1H-pyrrolo[2,3-b]pyridin-4-yl)-2,6-diazaspiro[3.4]octan-5-one Prepared according to the same protocol described in Scheme 2 to give 8 mg of the desired product in 19.52% yield. MS (ESI) m/z: 372.43 (M+H)+

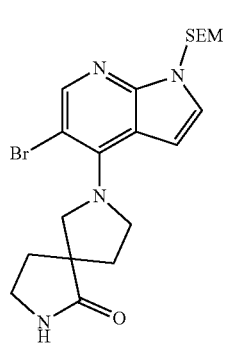 [SMILES: C[Si](C)(C)CCOCn1ccc2c(N3CCC4(CCNC4=O)C3)c(Br)cnc21]

7-(5-bromo-1-((2-(trimethylsilyl)ethoxy)methyl)-1H-pyrrolo[2,3-b]pyridin-4-yl)-2,7-diazaspiro[4.4]nonan-1-one Prepared according to the same protocol described in Scheme 1 to give 111 mg of the desired product in 43.4% yield (b.r.s.m.). MS (ESI) m/z: 468.17 (M+H)+

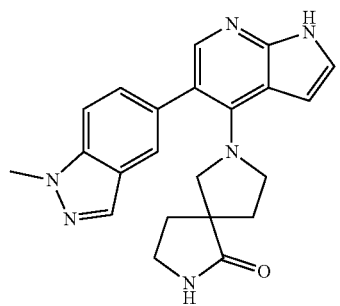 [SMILES: Cn1ncc2cc(-c3cnc4[nH]ccc4c3N3CCC4(CCNC4=O)C3)ccc21]

Compound 017: 7-(5-(1-methyl-1H-indazol-5-yl)-1H-pyrrolo[2,3-b]pyridin-4-yl)-2,7-diazaspiro[4.4]nonan-1-one Prepared according to the same protocol described in Scheme 2 to give 3.2 mg of the desired product in 7.73% yield. MS (ESI) m/z: 386.46 (M+H)+

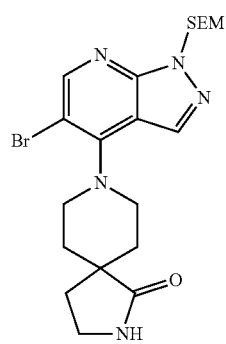 [SMILES: C[Si](C)(C)CCOCn1ncc2c(N3CCC4(CCNC4=O)CC3)c(Br)cnc21]

8-(5-bromo-1-((2-(trimethylsilyl)ethoxy)methyl)-1H-pyrazolo[3,4-b]pyridin-4-yl)-2,8-diazaspiro[4.5]decan-1-one Prepared according to the same protocol described in Scheme 1 to give 100 mg of the desired product in 37.7% yield. MS (ESI) m/z: 481.82 (M+H)+

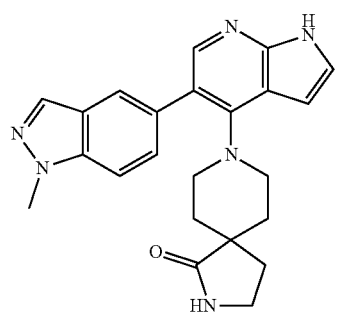 [SMILES: Cn1ncc2cc(-c3cnc4[nH]ccc4c3N3CCC4(CCNC4=O)CC3)ccc21]

Compound 001: 8-(5-(1-methyl-1H-indazol-5-yl)-1H-pyrrolo[2,3-b]pyridin-4-yl)-2,8-diazaspiro[4.5]decan-1-one Prepared according to the same protocol described in Scheme 2 to give 16 mg of the desired product. MS (ESI) m/z: 401.36 (M+H)+

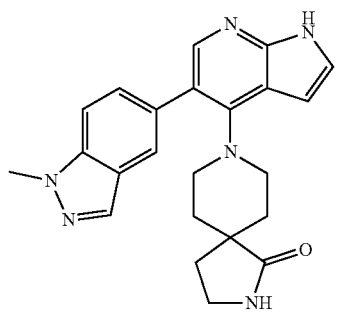 [SMILES: Cn1ncc2cc(-c3cnc4[nH]ccc4c3N3CCC4(CCNC4=O)CC3)ccc21]

Compound 015: 8-(5-(1-methyl-1H-indazol-5-yl)-1H-pyrazolo[3,4-b]pyridin-4-yl)-2,8-diazaspiro[4.5]decan-1-one Prepared according to the same protocol described in Scheme 2 to give 4.8 mg of the desired product in 4.42% yield. MS (ESI) m/z: 401.47 (M+H)+

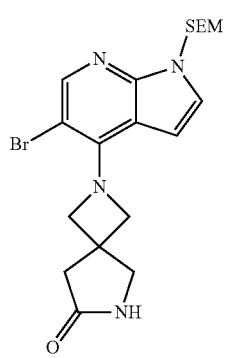 [SMILES: C[Si](C)(C)CCOCn1ccc2c(N3CC4(CNC(=O)C4)C3)c(Br)cnc21]

2-(5-bromo-1-((2-(trimethylsilyl)ethoxy)methyl)-1H-pyrrolo[2,3-b]pyridin-4-yl)-2,6-diazaspiro[3.4]octan-7-one Prepared according to the same protocol described in Scheme 1 to give 94 mg of the desired product in 62.8% yield. (b.r.s.m.). MS (ESI) m/z: 450.74 (M+H)+

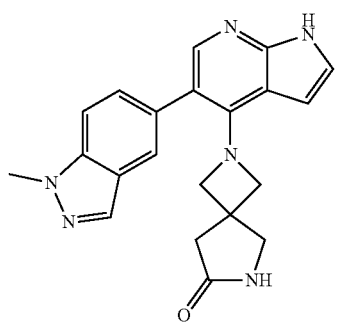 [SMILES: Cn1ncc2cc(-c3cnc4[nH]ccc4c3N3CC4(CNC(=O)C4)C3)ccc21]

Compound 013: 2-(5-(1-methyl-1H-indazol-5-yl)-1H-pyrrolo[2,3-b]pyridin-4-yl)-2,6-diazaspiro[3.4]octan-7-one Prepared according to the same protocol described in Scheme 2 to give 2 mg of the desired product in 4.88% yield. MS (ESI) m/z: 372.43 (M+H)+

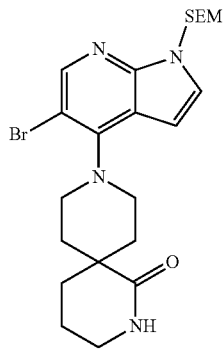 [SMILES: C[Si](C)(C)CCOCn1ccc2c(N3CCC4(CCCNC4=O)CC3)c(Br)cnc21]

9-(5-bromo-1-((2-(trimethylsilyl)ethoxy)methyl)-1H-pyrrolo[2,3-b]pyridin-4-yl)-2,9-diazaspiro[5.5]undecan-1-one Prepared according to the same protocol described in Scheme 1 to give 108 mg of the desired product in 60.9% yield (b.r.s.m.). MS (ESI) m/z: 492.74 (M+H)+ 1H NMR (500 MHz, CDCl3) δ 8.27 (s, 1H), 7.18 (d, J=5 Hz, 1H), 6.69 (d, J=5 Hz, 1H), 5.79 (s, 1H), 5.60 (s, 2H), 3.80-3.77 (m, 2H), 3.55-3.51 (m, 2H), 3.33 (m, 2H), 3.49-3.46 (m, 2H), 2.36-2.31 (m, 2H), 1.89-1.87 (m, 4H), 1.70-1.65 (m, 2H), 0.90 (t, J=10 Hz, 2H).

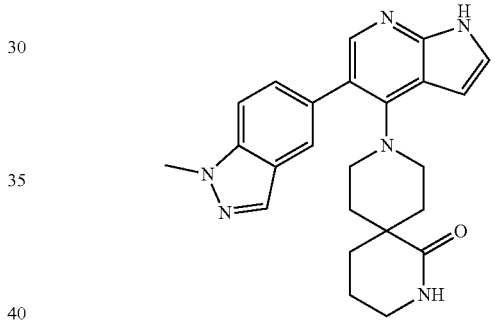

Compound 006: 9-(5-(1-methyl-1H-indazol-5-yl)-1H-pyrrolo[2,3-b]pyridin-4-yl)-2,9-diazaspiro[5.5]undecan-1-one Prepared according to the same protocol described in Scheme 2 to give 9.0 mg of the desired product in 21.71% yield. MS (ESI) m/z: 414.51 (M+H)+

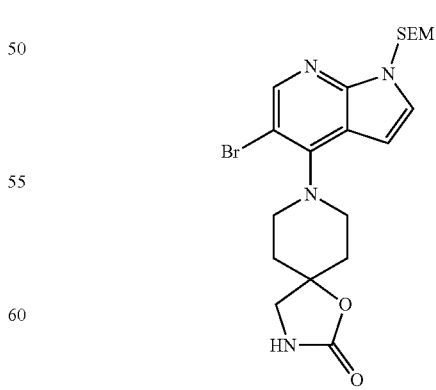

8-(5-bromo-1-((2-(trimethylsilyl)ethoxy)methyl)-1H-pyrrolo[2,3-b]pyridin-4-yl)-1-oxa-3,8-diazaspiro[4.5]decan-2-one Prepared according to the same protocol described in Scheme 1 to give 330 mg of the desired product in % yield (b.r.s.m.). MS (ESI) m/z: 483.1 (M+H)+

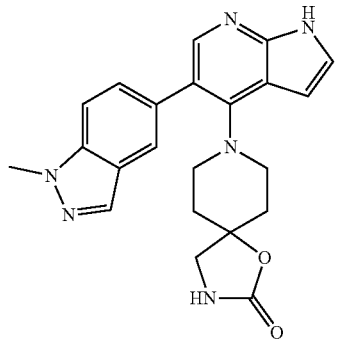 [SMILES: Cn1ncc2cc(-c3cnc4[nH]ccc4c3N3CCC4(CC3)CNC(=O)O4)ccc21]

Compound 011: 8-(5-(1-methyl-1H-indazol-5-yl)-1H-pyrrolo[2,3-b]pyridin-4-yl)-1-oxa-3,8-diazaspiro[4.5]decan-2-one Prepared according to the same protocol described in Scheme 2 to give 2.5 mg of the desired product in 2.0% yield. MS (ESI) m/z: 402.46 (M+H)+

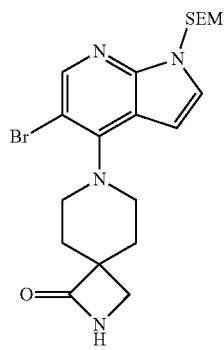 [SMILES: C[Si](C)(C)CCOCn1ccc2c(N3CCC4(CC3)CNC4=O)c(Br)cnc21]

7-(5-bromo-1-((2-(trimethylsilyl)ethoxy)methyl)-1H-pyrrolo[2,3-b]pyridin-4-yl)-2,7-diazaspiro[3.5]nonan-1-one Prepared according to the same protocol described in Scheme 2 to give 48 mg of the desired product in 37.3% yield (b.r.s.m.). MS (ESI) m/z: 467.13 (M+H)+ 1H NMR (500 MHz, CDCl3) δ 8.30 (s, 1H), 7.21 (d, J=5 Hz, 1H), 6.66 (d, J=5 Hz, 1H), 5.79 (s, 1H), 5.63 (s, 2H), 3.82-3.78 (m, 2H), 3.55-3.48 (m, 2H), 2.26-2.21 (m, 2H), 2.07-2.02 (m, 2H), 0.90 (t, J=10 Hz, 2H).

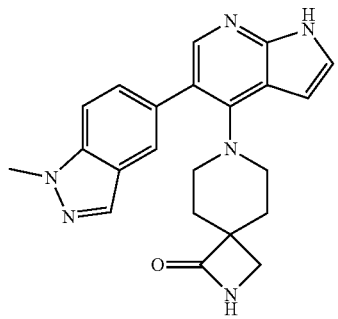 [SMILES: Cn1ncc2cc(-c3cnc4[nH]ccc4c3N3CCC4(CC3)CNC4=O)ccc21]

Compound 010: 7-(5-(1-methyl-1H-indazol-5-yl)-1H-pyrrolo[2,3-b]pyridin-4-yl)-2,7-diazaspiro[3.5]nonan-1-one Prepared according to the same protocol described in Scheme 2 to give 1.5 mg of the desired product in 1.76% yield. MS (ESI) m/z: 386.46 (M+H)30

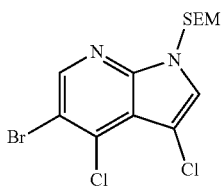 [SMILES: C[Si](C)(C)CCOCn1cc(Cl)c2c(Cl)c(Br)cnc21]

5-bromo-3,4-dichloro-1-((2-(trimethylsilyl)ethoxy)methyl)-1H-pyrrolo[2,3-b]pyridine Prepared according to the same protocol described in Scheme 1 to give 5.5 g of the desired product in 73.3% yield. MS (ESI) m/z: 396.97 (M+H)+ 1H NMR (500 MHz, DMSO-d6) δ 8.57 (s, 1H), 8.07 (s, 1H), 5.60 (s, 2H), 3.51 (t, J=10 Hz, 2H), 0.81 (t, J=10 Hz, 2H).

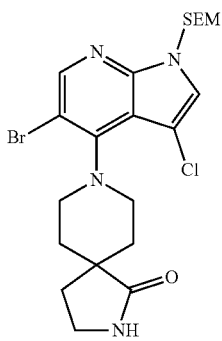 [SMILES: C[Si](C)(C)CCOCn1cc(Cl)c2c(N3CCC4(CCNC4=O)CC3)c(Br)cnc21]

8-(5-bromo-3-chloro-1-((2-(trimethylsilyl)ethoxy)methyl)-1H-pyrrolo[2,3-b]pyridin-4-yl)-2,8-diazaspiro[4.5]decan-1-one Prepared according to the same protocol described in Scheme 1 to give 200 mg of the desired product in 64.3% yield (b.r.s.m.). MS (ESI) m/z: 514.10 (M+H)+ 1H NMR (500 MHz, CDCl3) δ 8.35 (s, 1H), 7.26 (s, 1H), 5.63 (s, 2H), 3.65-3.60 (m, 2H), 3.57-3.54 (m, 2H), 3.42-3.39 (m, 4H), 2.31-2.26 (m, 2H), 2.25-2.22 (m, 2H), 1.57 (d, J=10 Hz, 2H), 0.91 (t, J=10 Hz, 2H).

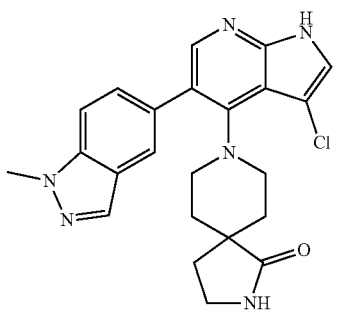 [SMILES: Cn1ncc2cc(-c3cnc4[nH]cc(Cl)c4c3N3CCC4(CCNC4=O)CC3)ccc21]

Compound 018: 8-(3-chloro-5-(1-methyl-1H-indazol-5-yl)-1H-pyrrolo[2,3-b]pyridin-4-yl)-2,8-diazaspiro[4.5]decan-1-one Prepared according to the same protocol described in Scheme 2 to give 20 mg of the desired product in 12.2% yield. MS (ESI) m/z: 435.21 (M+H)+ 1H NMR (500 MHz, DMSO-d$_6$) δ 8.09 (s, 1H), 7.96 (s, 1H), 7.70 (s, 1H), 7.68 (s, 1H), 7.59 (s, 1H), 7.49 (s, 1H), 7.35 (d, J=10 Hz, 1H), 4.10 (s, 3H), 3.12-3.10 (m, 2H), 3.08-3.05 (m, 2H), 2.73-2.69 (m, 2H), 1.85-1.80 (m, 2H), 1.72-1.70 (m, 2H), 1.21 (s, 1H), 1.19-1.16 (m, 2H).

Example 3—Synthetic Procedure C

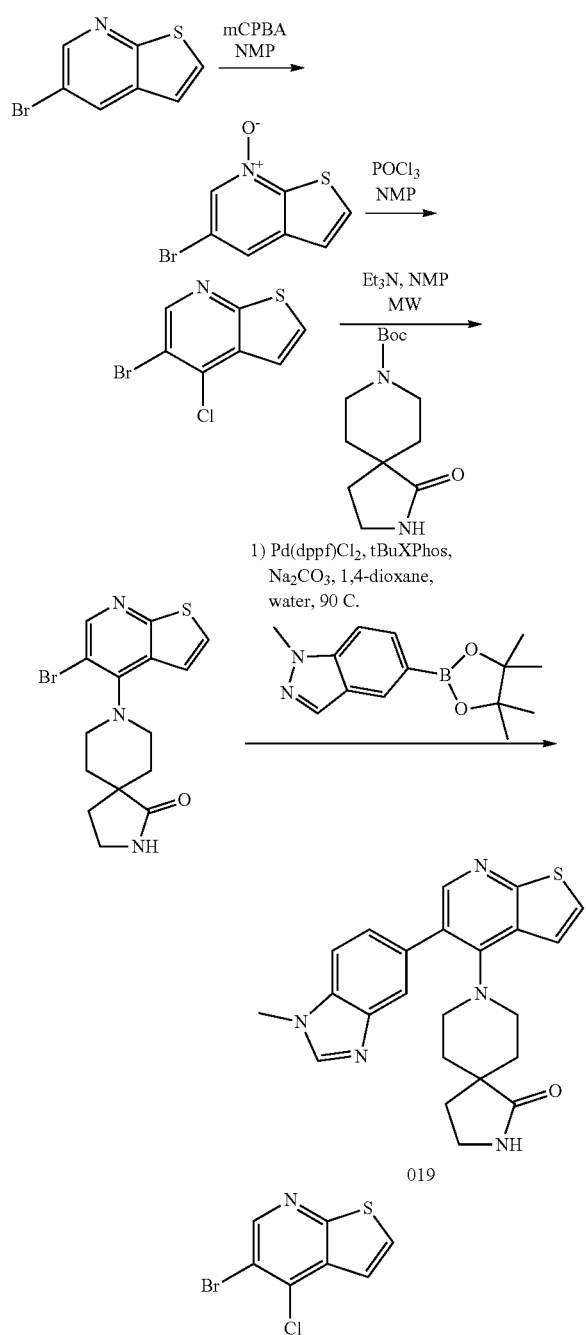

5-bromo-4-chlorothieno[2,3-b]pyridine

To a 0° C. solution of 5-bromothieno[2,3-b]pyridine (1 g, 4.67 mmol) in NMP (20 mL) was added mCPBA (1.3 g, 5.60 mmol), and the mixture warmed to rt and stirred for 2 days. The reaction was quenched with sat. aq. NaHCO$_3$ and extracted with EtOAc. The combined aqueous layer was washed with brine, dried over MgSO$_4$ and condensed to give a brown oil that was dissolved in NMP (20 mL) and cooled to 0° C. POCl$_3$ (0.873 mL, 9.34 mmol) was added dropwise and the mixture stirred at 0° C. for 1 hr. The mixture was poured into ice-water and slowly neutralized with sat. aq. NaHCO$_3$. The mixture was extracted with EtOAc, washed with brine, dried over MgSO$_4$ and condensed to give a light-yellow solid that was used without further purification. MS (ESI) m/z: 249.76 (M+H)$^+$

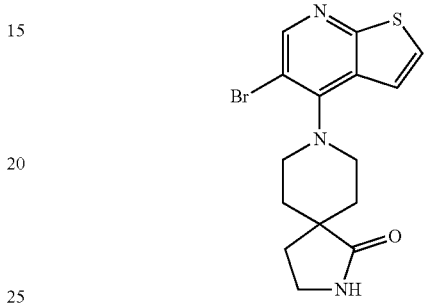

8-(5-bromothieno[2,3-13]pyridin-4-yl)-2,8-diazaspiro[4.5]decan-1-one

Prepared according to the same protocol described in Scheme 1 to give 270 mg of the desired product in 36.6% yield. MS (ESI) m/z: 367.98 (M+H)$^+$

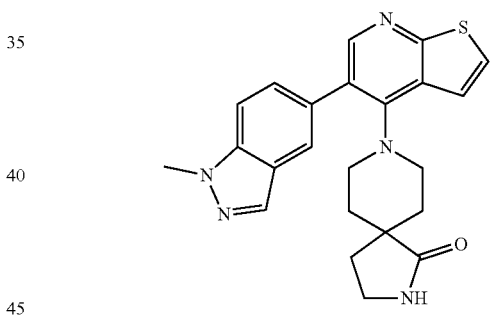

Compound 019: 8-(5-(1-methyl-1H-indazol-5-yl)thieno[2,3-b]pyridin-4-yl)-2,8-diazaspiro[4.5]decan-1-one Prepared according to the same protocol described in Scheme 2 to give 11 mg of the desired product in 19.2% yield. MS (ESI) m/z: 418.18 (M+H)$^+$ Example 4—CDK8 Inhibition The inhibitory activity of the compounds disclosed herein were tested using LanthaScreen® Eu Kinase Binding Assay for CDK8/cyclin C from Invitrogen. Optimization of the tracer concentration was performed using the following protocol.

The reagent was prepared through a series of dilutions of the tracer. The tracer was first diluted to 3000 nM by adding 3.6 µL of 50 µL stock tracer to 56 µL of 1× Kinase Buffer A. 50 µL of 1× Kinase Buffer A was added to 5 wells in each of two columns of a 96-well plate. 50 µL of the 3000 nM tracer was added to well A1 and mixed. 50 µL of solution was removed from A1 and transferred to A2 and mixed. 50 µL of the solution in well A2 was removed and transferred to well B1 and mixed. This protocol was repeated nine times to the desired concentration. The kinase/antibody solution was prepared at 15 nM kinase, 6 nM antibody, and 6 nM Eu-Streptavidin. Both the antibody tube and Eu-Streptavidin tube were centrifuged at approximately 10,000×g for ten minutes, and the desired volume was aspirated from the top. The volume of reagents added to Kinase Buffer A were calculated using the equations provided in the LanthaScreen® Eu Kinase Binding Assay Validation Packet. 30 µM staurosporine ("competitor solution") was prepared by diluting 30 µL of 1 mM staurosporine (from a stock in DMSO) into 970 µL Kinase Buffer A. A 3% DMSO control solution was prepared by adding 30 µL DMSO to 970 µL Kinase Buffer A.

5 µL of each concentration of serially diluted tracer was added to six replicate assay wells in a 384-well plate. 5 µL of competitor solution was added to three wells for each tracer concentration. 5 µL of DMSO control solution was added to the other three wells for each tracer concentration. 5 µL of kinase/antibody solution was added to all wells, and the plate was incubated at room temperature for 60 mins.

The "emission ratio" was calculated by dividing the acceptor/tracer emission (665 nm) by the antibody/donor emission (615 nm). The concentration of tracer versus emission ratio was plotted for the competitor (staurosporine) and control (DMSO). The sigmoidal dose-response curve with a variable slope was fitted to the data using GraphPad™ Prism software.

The $IC_{50}$ values of the compounds disclosed herein were determined using the following procedure which generates a 10-point $IC_{50}$ curve from a 4-fold dilution series of test compound. The concentration of tracer used is based on the tracer titration from the procedure above.

The reagent was prepared by a series of dilutions of each test compound by 4× serial dilution in DMSO such that the concentration was 1 mM. 4 mM solution of the test compound was prepared in DMSO. 60 µL of DMSO was added to five wells in each of two columns of a 96-well plate. 20 µL of the 4 mM compound solution was added to well A1 and mixed. 20 µL of solution was removed from A1 and transferred to A2 and mixed. 20 µL of the solution in well A2 was removed and transferred to well B1 and mixed. This protocol was repeated six times to the desired concentration.

The "master dilution" series was diluted 33.3-fold into Kinase Buffer A. 5 µL were removed from each concentration of diluted compound, and transferred to another 96-well plate. 162 µL of Kinase Buffer A was added and the two solutions were mixed together. A tracer solution was prepared in Kinase Buffer A at 30 nM tracer. The volume of reagents added to Kinase Buffer A were calculated using the equations provided in the LanthaScreen® Eu Kinase Binding Assay Validation Packet.

The kinase/antibody solution was prepared at 15 nM kinase, 6 nM antibody, and 6 nM Eu-Streptavidin. The antibody tube and Eu-Streptavidin tube were centrifuged at 10,000×g for 10 minutes, and the desired volume was aspirated from the top of the solution. 5 µL of each concentration of serially diluted compound were added to triplicate assay wells in a 384-well plate. 5 µL of the kinase/antibody solution and 5 µL of the tracer solution were added to all wells. The plate incubated at room temperature for 60 min and read.

The "emission ratio" was calculated by dividing the acceptor/tracer emission (665 nm) by the antibody/donor emission (615 nm). The concentration of test compound versus emission ratio was plotted. The sigmoidal dose-response curve with a variable slope was fitted to the data using GraphPad™ Prism software.

| Compound No. | CDK8 $IC_{50}$ (nM) |
| --- | --- |
| 001 | 2 |
| 002 | 6.46 |
| 003 | 7.00 |
| 004 | 24.5 |
| 005 | 32.2 |
| 006 | 3 |
| 007 | 274.0 |
| 008 | 4.97 |
| 009 | 76.4 |
| 010 | 6.3 |
| 011 | 7 |
| 012 | 916 |
| 013 | 538 |
| 014 | 3 |
| 015 | 547 |
| 016 | 10 |
| 017 | 55 |
| 018 | 1.73 |
| 019 | 206 |
| 020 | 1.37 |
| 021 | 36 |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:
1. A compound of Formula I:

(I)

or a pharmaceutically acceptable salt thereof;
wherein:
  ═ is an optional double bond;
  A is a 5-8 membered heteroaryl;
  B is CH or N;
  D is $CR^5$ or N;
  X is C or N;
  Y is C or N;
  Z is NH, S, or O;
  $R^1$ and $R^2$, together with the carbon to which they are attached, form a 4-6 membered heterocyclic ring that is substituted one or two times with $R^4$;

R³ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;

R⁴ is selected from the group consisting of absent, =O, amino, and hydroxy;

R⁵ is selected from the group consisting of hydrogen, halo, CN, $C_3$-$C_6$ cycloalkyl, and $C_1$-$C_6$ alkyl, wherein $C_1$-$C_6$ alkyl is optionally substituted by 1, 2, or 3 halo; and m is 1, 2, or 3.

2. The compound according to claim 1, wherein the compound of Formula I is a compound of Formula II:

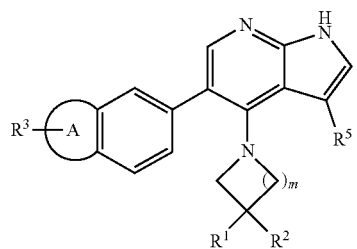

(II)

or a pharmaceutically acceptable salt thereof.

3. The compound according to claim 1, wherein R¹ and R², together with the carbon to which they are attached, form piperidinone, pyrrolidinone, azetidinone, oxazolidinone, imidazolidine-dione, dihydro-thiazole, dihydro-oxazole, dihydro-pyrrole, dihydro-imidazolone, or morpholinone.

4. The compound according to claim 1, wherein A is selected from the group consisting of pyrazole, thiazole, imidazole, and triazole.

5. A compound of Formula III:

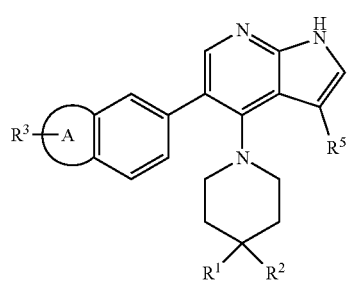

(III)

or a pharmaceutically acceptable salt thereof;
wherein:
A is a 5-8 membered heteroaryl;
R¹ and R², together with the carbon to which they are attached, form a 4-6 membered heterocyclic ring that is substituted one or two times with R⁴;
R³ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;
R⁴ is selected from the group consisting of absent, =O, amino, and hydroxy; and
R⁵ is selected from the group consisting of hydrogen, halo, CN, $C_3$-$C_6$ cycloalkyl, and $C_1$-$C_6$ alkyl, wherein $C_1$-$C_6$ alkyl is optionally substituted by 1, 2, or 3 halo.

6. The compound according to claim 5, wherein the compound of Formula III is a compound of Formula IIIa:

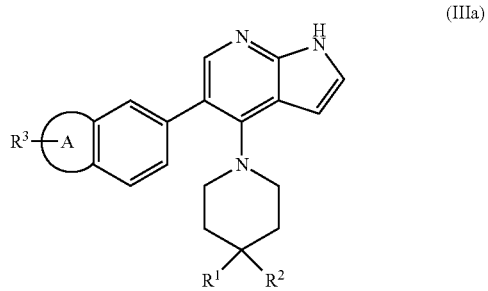

(IIIa)

or a pharmaceutically acceptable salt thereof.

7. The compound according to claim 5, wherein the compound of Formula III is a compound of Formula IV:

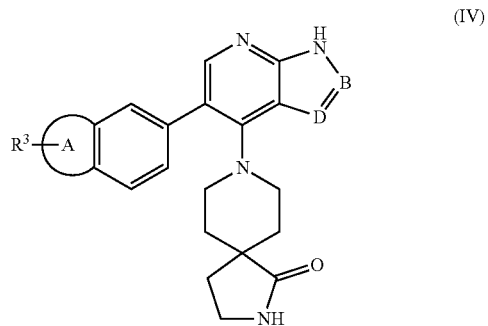

(IV)

or a pharmaceutically acceptable salt thereof.

8. The compound according to claim 1, wherein the compound of Formula I is a compound of Formula V:

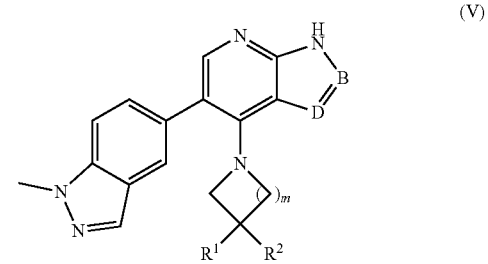

(V)

or a pharmaceutically acceptable salt thereof.

9. The compound according to claim 1, wherein B and D are both CH.

10. The compound according to claim 1, wherein B is N and D is CH.

11. The compound according to claim 1, wherein B is CH and D is N.

12. The compound according to claim 1 wherein B is CH and D is CR⁵.

13. The compound according to claim 1, wherein the compound of Formula I is a compound of Formula VI:

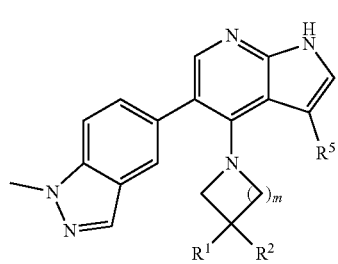

(VI)

or a pharmaceutically acceptable salt thereof.

14. A compound of Formula VIII:

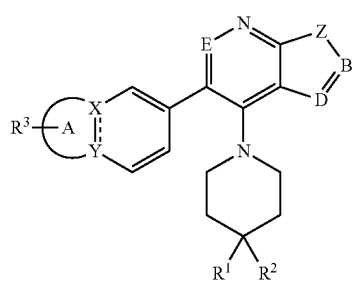

(VIII)

or a pharmaceutically acceptable salt thereof;
wherein:
═ is an optional double bond;
A is a 5-8 membered heteroaryl;
B and D are each independently $CR^5$ or N;
E is CH or N;
X is C or N;
Y is C or N;
Z is NH, S, or O;
$R^1$ and $R^2$, together with the carbon to which they are attached, form a 4-6 membered heterocyclic ring that is substituted one or two times with $R^4$;
$R^3$ is selected from the group consisting of absent, halo, hydroxy, cyano, $C_1$-$C_6$ alkyl, $C_1$-$C_6$ alkoxy, and $C_3$-$C_6$ cycloalkyl, wherein $C_1$-$C_6$ alkyl is optionally substituted by 1, 2, or 3 halo;
$R^4$ is selected from the group consisting of absent, ═O, amino, and hydroxy; and
each $R^5$ is independently selected from the group consisting of hydrogen, halo, CN, $C_3$-$C_6$ cycloalkyl, and $C_1$-$C_6$ alkyl, wherein $C_1$-$C_6$ alkyl is optionally substituted by 1, 2, or 3 halo.

15. The compound of claim 14, wherein the compound of Formula VIII is a compound of Formula VIIIa:

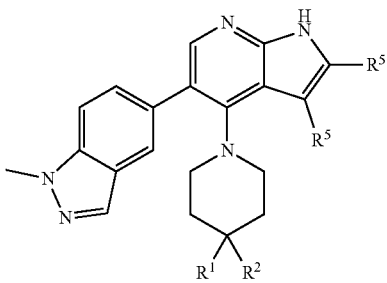

(VIIIa)

or a pharmaceutically acceptable salt thereof.

16. The compound of claim 14, wherein the compound of Formula VIII is a compound of Formula VIIIb:

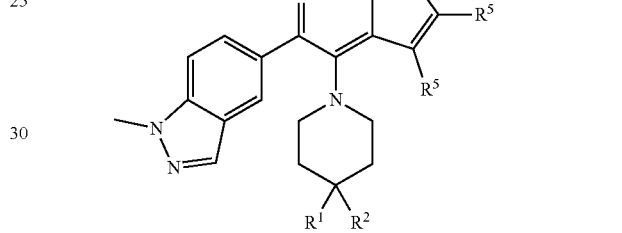

(VIIIb)

or a pharmaceutically acceptable salt thereof.

17. The compound according to claim 1 wherein $R^1$ and $R^2$, together with the atoms to which they are attached, form one of the following heterocyclic rings

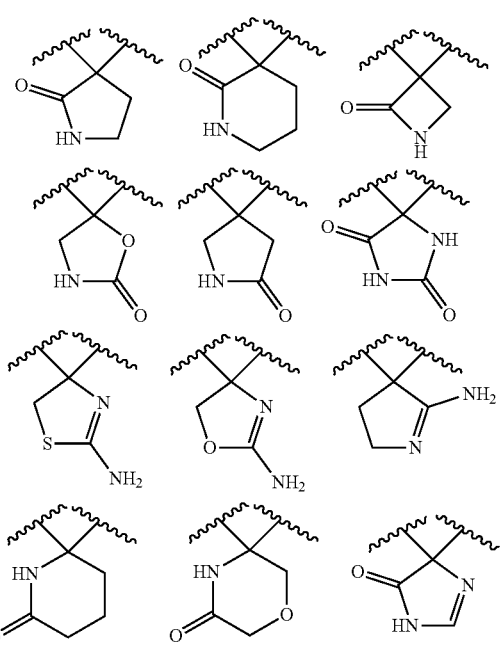

18. The compound according to claim 14, wherein the compound of Formula VIII is selected from the group consisting of
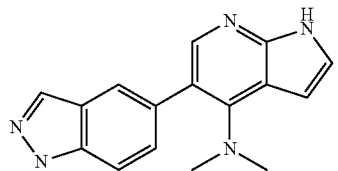
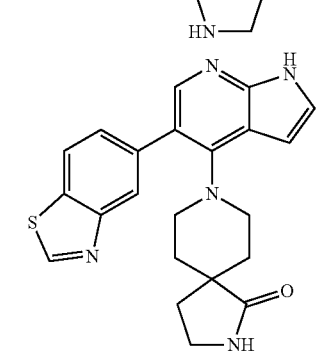
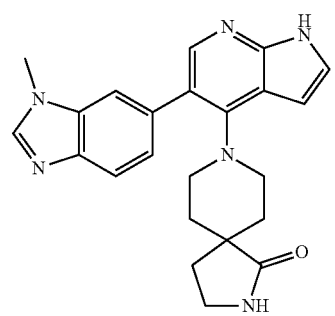
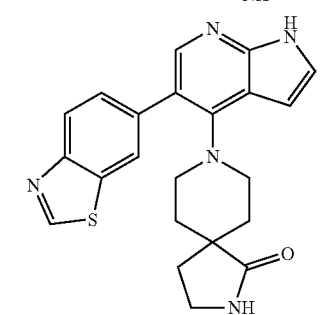
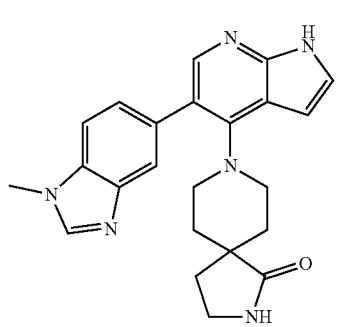
-continued
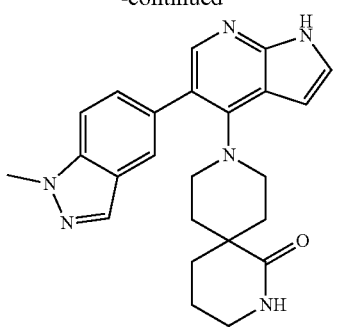
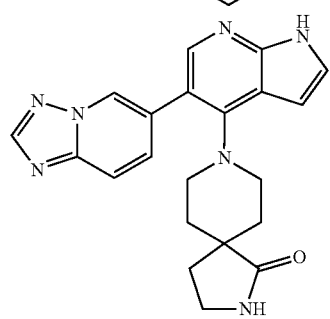
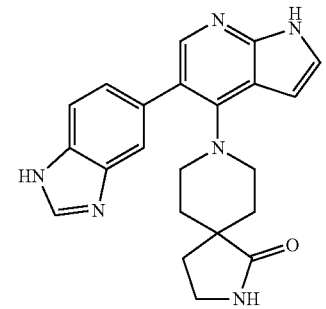
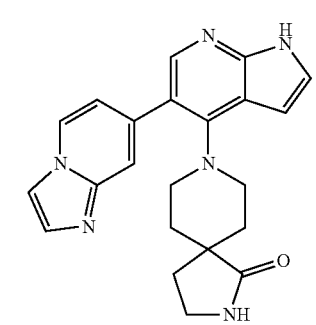
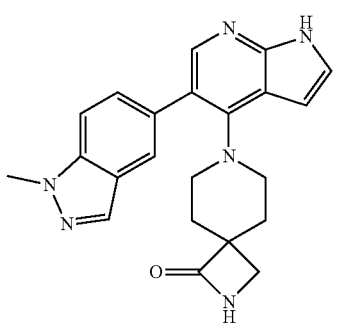

-continued

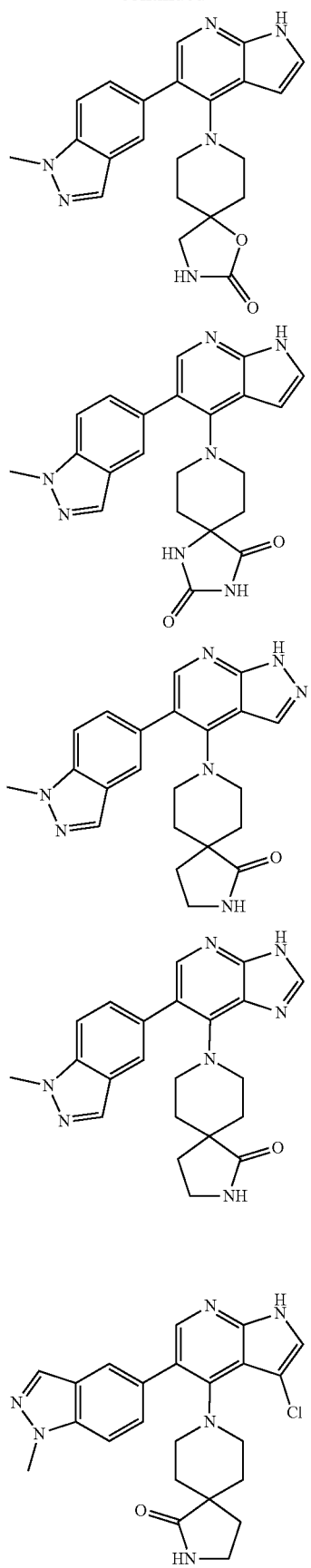

-continued

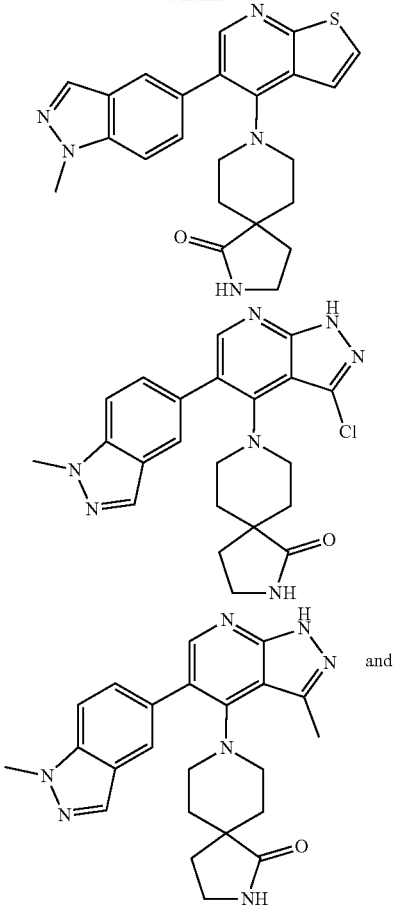

or a pharmaceutically acceptable salt thereof.

19. A pharmaceutical composition comprising a compound according to claim 1 and a pharmaceutically acceptable carrier.

20. A method of inhibiting cyclin-dependent kinase 8 (CDK8) and cyclin-dependent kinase 19 (CDK19) in a subject in need thereof comprising administering to the subject a therapeutically effective amount of a compound according to claim 1.

21. A method of treating a proliferative disease in a subject in need thereof comprising administering to the subject a therapeutically effective amount of a compound according to claim 1.

22. A method of treating a cyclin-dependent kinase 8 (CDK8)-mediated disease and/or a cyclin-dependent kinase 19 (CDK19)-mediated disease in a subject in need thereof comprising administering to the subject a therapeutically effective amount of a compound according to claim 1, wherein the disease is cancer or a neurodegenerative disorder.

23. The method of claim 22, wherein the cancer is selected from the group consisting of lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma, lymphomas, myelomas, melanoma and solid tumors.

24. The method of claim 22, wherein the cancer is selected from the group consisting of leukemia, lymphoma, colorectal cancer, epithelial call-derived neoplasia (epithelial carcinoma), basal cell carcinoma, adenocarcinoma, gastrointestinal cancer, lip cancer, mouth cancer, esophageal cancer, small bowel cancer, bladder cancer, cervical cancer, squamous cell and/or basal cell cancers, renal cell carcinoma, and B-Cell Lymphoma.

25. The method of claim 24, wherein the leukemia is selected from the group consisting of chronic myelogenous leukemia (CML), acute myeloid leukemia (AML) and acute promyelocytic leukemia (APL).

26. The method of claim 22, wherein the neurodegenerative disorder is selected from the group consisting of Alzheimer's disease, Parkinson's disease, Huntington's disease, amyotrophic lateral sclerosis, spinal cord injury, and peripheral neuropathy.

27. The compound of claim 1, wherein the compound of Formula I is selected from the group consisting of

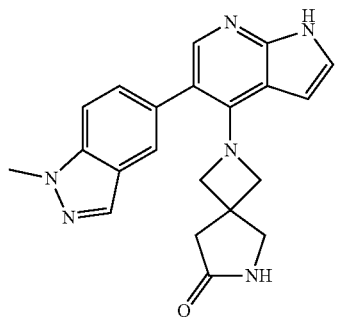

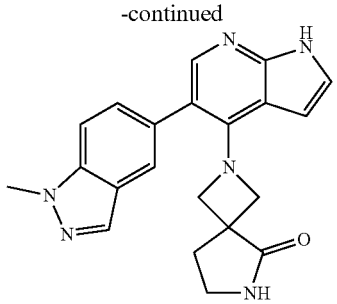

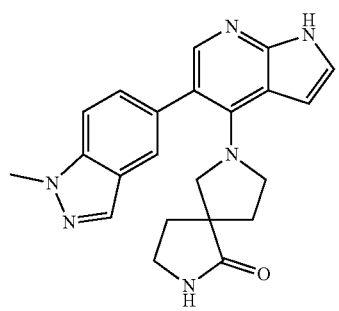

and or a pharmaceutically acceptable salt thereof.

* * * * *